US009285333B2

(12) United States Patent
Watanabe et al.

(10) Patent No.: US 9,285,333 B2
(45) Date of Patent: Mar. 15, 2016

(54) COMBUSTIBLE GAS DETECTION DEVICE

(75) Inventors: Masaya Watanabe, Komaki (JP); Shoji Kitanoya, Kasugai (JP); Daisuke Ichikawa, Kani (JP); Masahiro Yamashita, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 267 days.

(21) Appl. No.: 13/978,038

(22) PCT Filed: Feb. 9, 2012

(86) PCT No.: PCT/JP2012/052969
§ 371 (c)(1),
(2), (4) Date: Jul. 2, 2013

(87) PCT Pub. No.: WO2012/108500
PCT Pub. Date: Aug. 16, 2012

(65) Prior Publication Data
US 2013/0298638 A1    Nov. 14, 2013

(30) Foreign Application Priority Data

Feb. 9, 2011  (JP) ................................. 2011-025754
Dec. 27, 2011 (JP) ................................. 2011-286387

(51) Int. Cl.
*G01N 27/18* (2006.01)
*H01M 8/04* (2006.01)

(52) U.S. Cl.
CPC ........... *G01N 27/18* (2013.01); *H01M 8/04447* (2013.01); *H01M 2250/20* (2013.01); *Y02E 60/50* (2013.01); *Y02T 90/32* (2013.01)

(58) Field of Classification Search
CPC ............. G01N 27/18; H01M 8/04447; H01M 2250/20; Y02E 60/50; Y02T 90/32
USPC ........................................................ 73/23.31
See application file for complete search history.

(56) References Cited

U.S. PATENT DOCUMENTS 4,210,024 A * 7/1980 Ishiwatari ............ G01D 3/0365
                                                    374/1
5,551,283 A    9/1996 Manaka et al.
(Continued)

FOREIGN PATENT DOCUMENTS

JP    06-3312 A    1/1994
JP    07-055748 A  3/1995
(Continued)

OTHER PUBLICATIONS

International Search Report mailed May 15, 2012 for the corresponding PCT Application No. PCT/JP2012/052969.
(Continued)

*Primary Examiner* — Daniel S Larkin
(74) *Attorney, Agent, or Firm* — Leason Ellis LLP

(57) ABSTRACT

A combustible gas detection device includes an energization control circuit which controls the switching of the energization state of a heat generation resistor every predetermined time period such that the heat generation resistor alternately has resistances corresponding to two predetermined temperatures, a temperature measurement resistor disposed on the same substrate on which the heat generation resistor is disposed, where its resistance changes with the environmental temperature, a gas concentration computation section which calculates the combustible gas concentration by using a voltage generated across the heat generation resistor which is detected when electricity is supplied to the heat generation resistor and the environmental temperature based on a voltage change caused by a change in the resistance of the temperature measurement resistor. The predetermined time period is such that a change in the environmental temperature which occurs when the energization control circuit switches the energization state, falls within a range of 0.5° C.

13 Claims, 12 Drawing Sheets

(56) References Cited

U.S. PATENT DOCUMENTS

2008/0282771 A1 11/2008 Hamatani et al.
2011/0257897 A1 10/2011 Watanabe et al.

FOREIGN PATENT DOCUMENTS

| JP | 10-197305 A | 7/1998 |
|---|---|---|
| JP | 2001-264279 A | 9/2001 |
| JP | 2004-286492 A | 10/2004 |
| JP | 2006-010670 A | 1/2006 |
| JP | 2008-180542 A | 8/2008 |
| JP | 4302611 B2 | 5/2009 |
| JP | 2010-091299 A | 4/2010 |
| JP | 2011-237407 A | 11/2011 |

OTHER PUBLICATIONS

Office Action mailed Apr. 8, 2014 for the related Japanese Patent Application No. 2012-535515.
Japanese Office Action mailed Nov. 26, 2013 for the related Japanese Patent Application No. 2012-535515.

* cited by examiner

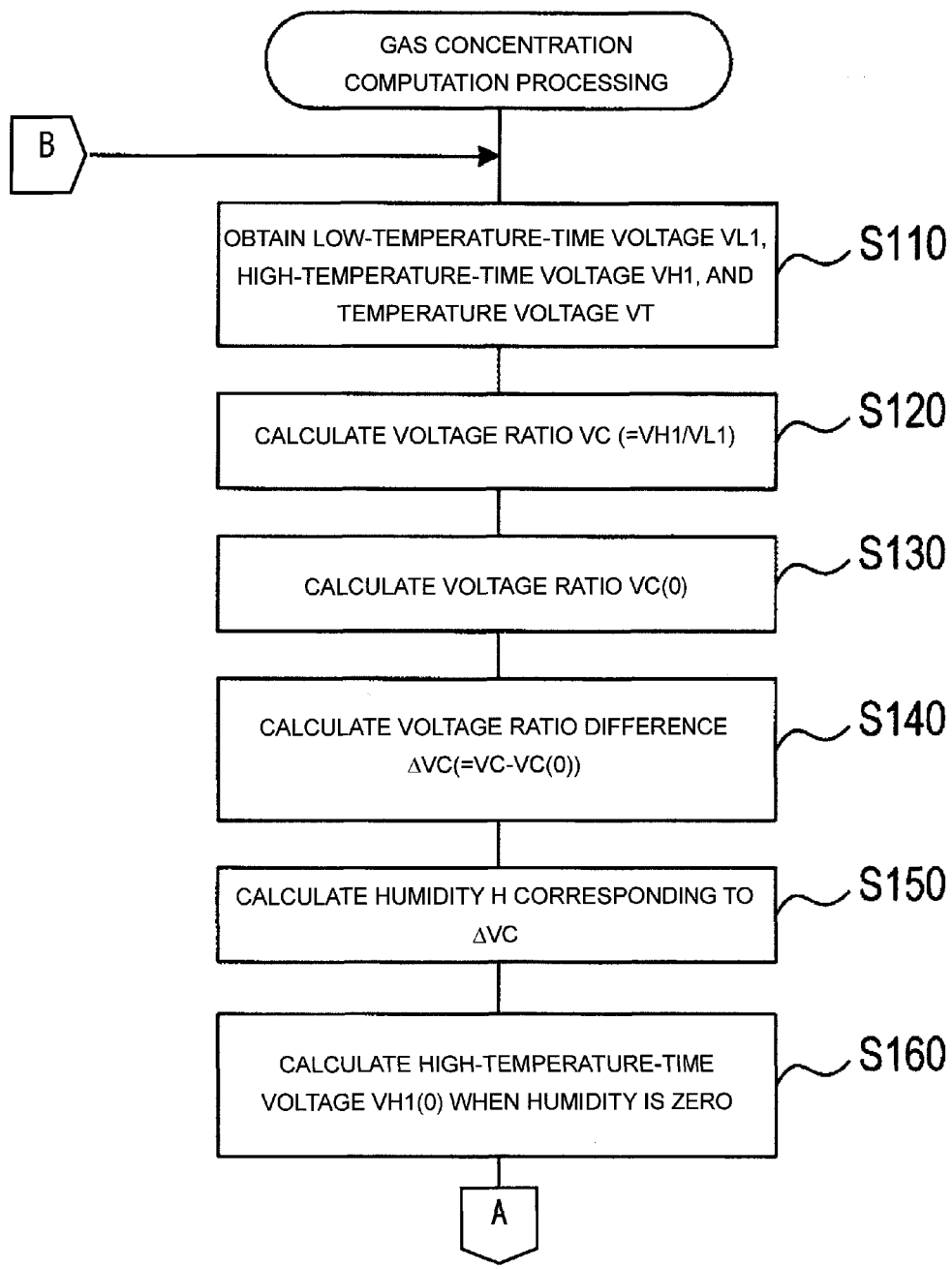

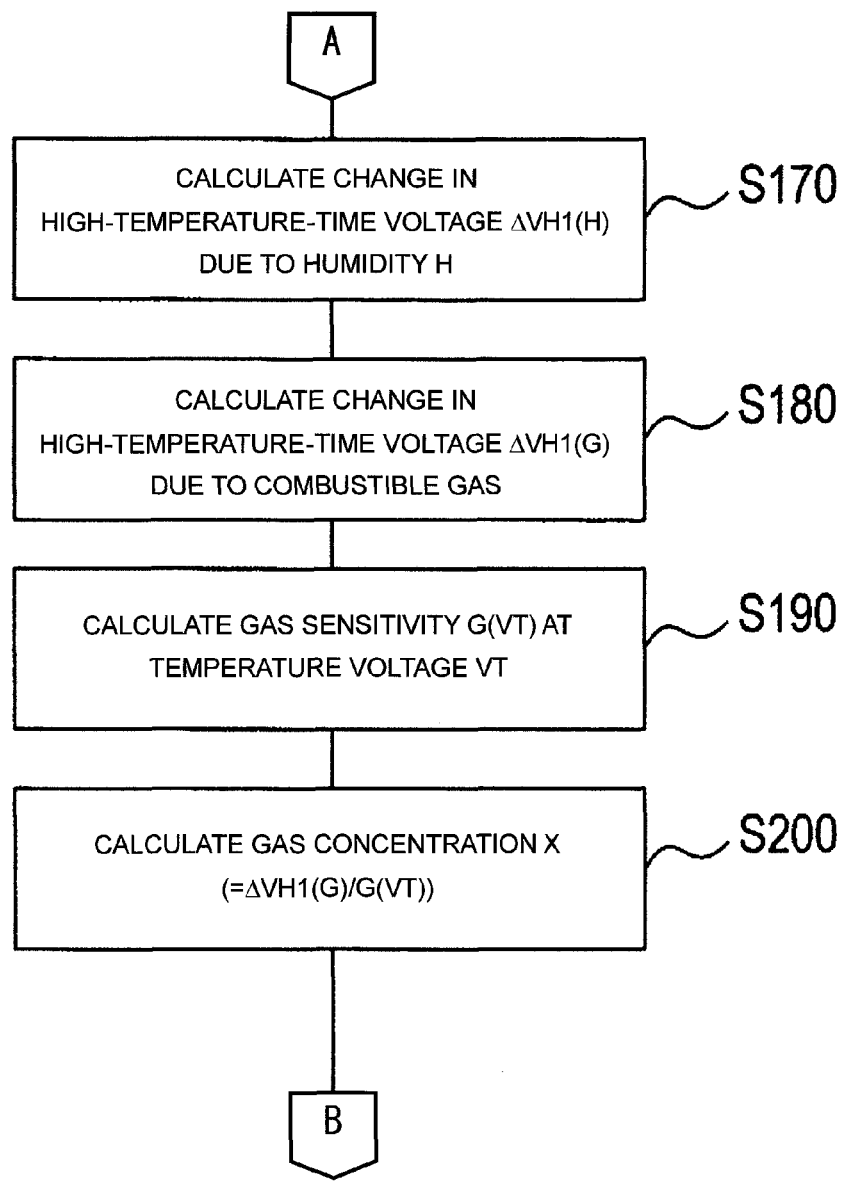

COMBUSTIBLE GAS DETECTION DEVICE

CROSS-REFERENCE TO RELATED PATENT APPLICATIONS

This application is a U.S. National Phase Application under 35 U.S.C. §371 of International Patent Application No. PCT/JP2012/052969, filed Aug. 18, 2011, and claims the benefit of Japanese Patent Application No. 2011-286387, filed on Dec. 27, 2011 and Japanese Patent Application No. 2011-025754 filed on Feb. 9, 2011, all of which are incorporated by reference in their entirety herein. The International Application was published in Japanese on Aug. 16, 2012 as International Publication No. WO/2012/108500 under PCT Article 21(2).

FIELD OF THE INVENTION

The present invention relates to a combustible gas detection device which detects the concentration of a combustible gas present in an object atmosphere.

BACKGROUND OF THE INVENTION

In recent years, in order to satisfy social needs such as protection of environment and nature, researches have been actively conducted on fuel cells which are efficient and clean energy sources. Among them, polymer electrolyte fuel cells (PEFC) and hydrogen internal combustion engines are expected as energy sources for homes, vehicles, etc. because they can operate at low temperature and are high in output density.

In these systems, detection of gas leakage is important because these systems use hydrogen which is a combustible gas as fuel.

There has been known a combustible gas detection device which detects the concentration of such a combustible gas present in an object atmosphere. The known combustible gas detection device includes a gas detection element which is disposed in an object atmosphere and which includes a heat generation resistor and a temperature measurement resistor provided thereon. The resistance of the heat generation resistor changes due to a change in the temperature of the heat generation resistor itself (due to heat generation of the heat generation resistor). The resistance of the temperature measurement resistor changes due to a change in the environmental temperature.

Specifically, in this combustible gas detection device, the resistance of the heat generation resistor in the gas detection element is controlled through use of a bridge circuit such that the resistance alternately becomes equal to resistances corresponding to two set temperature (first and second set temperatures), and the concentration of the combustible gas is calculated from control voltages (voltages across the heat generation resistor) at that time and a voltage difference (temperature voltage) produced as a result of a change in the resistance of the temperature measurement resistor.

The switching between the two set temperatures (first and second set temperatures) is performed, for example, by alternately selecting fixed resistors which are provided in the bridge circuit and have different resistances every time a predetermined period of time elapses (see, for example, Japanese Patent No. 4302611).

Incidentally, with recent progress of the integration technique, the degree of miniaturization of gas detection elements increases. As a result, in the combustible gas detection device, the heat generation resistor and the temperature measurement resistor tend to be disposed closer to each other as compared with conventional gas detection elements.

In the conventional combustible gas detection device, the influence of a change in the heat generation temperature of the heat generation resistor (i.e., the difference between the first set temperature and the second set temperature) on the temperature measurement resistor is not considered. Therefore, because of this influence, an error is produced between the actual environmental temperature and the environmental temperature determined on the basis of the temperature voltage of the temperature measurement resistor, whereby the accuracy in detecting the gas concentration decreases.

SUMMARY OF THE INVENTION

In order to solve the above-described problem, the present invention provides a combustible gas detection device which can suppress the lowering of accuracy in detecting the concentration of a gas, and also provides a combustible gas detection device which can accurately detecting the concentration of a gas.

A combustible gas detection device according to a first aspect of the present invention comprises a heat generation resistor disposed in an object atmosphere where its resistance changes with its own temperature; an energization control section which controls the switching the energization state of the heat generation resistor every time a predetermined time period elapses such that the heat generation resistor alternately has resistances corresponding to two predetermined temperatures set in advance; and a temperature measurement resistor disposed on a substrate having the heat generation resistor disposed thereon where its resistance changes with an environmental temperature which is the temperature of the object atmosphere.

The combustible gas detection device includes a gas concentration computation section which computes the concentration of a combustible gas contained in the object atmosphere by using a voltage generated across the heat generation resistor which is detected when electricity is supplied to the heat generation resistor by the energization control section, and using the environmental temperature based on a voltage difference (temperature voltage) which occurs as a result of a change in the resistance of the temperature measurement resistor.

According to the present embodiment, in such a configuration, the length of the predetermined time period is set in advance such that a change in the environmental temperature which occurs when the energization control section switches the energization state of the heat generation resistor falls within a range of 0.5° C.

According to the combustible gas detection device configured as described above, the heat generation temperature (predetermined temperature) of the heat generation resistor is switched before the error between the actual environmental temperature and the environmental temperature based on the temperature voltage of the temperature measurement resistor increases. As a result, the detection error of the gas concentration can be decreased to fall within the allowable range, and a drop in the accuracy in detecting the concentration of the combustible gas can be suppressed.

In the combustible gas detection device according to a second aspect of the present invention, the two predetermined temperatures are a first predetermined temperature and a second predetermined temperature lower than the first predetermined temperature, the first and second predetermined temperatures being set in advance such that the difference between the first and second predetermined temperatures becomes 50° C. or greater. The gas concentration computation section determines the voltage across the heat generation resistor detected at the first predetermined temperature as a high-temperature-time voltage, determines the voltage across the heat generation resistor detected at the second predetermined temperature as a low-temperature-time voltage, calculates a humidity of the object atmosphere based on a ratio between the high-temperature-time voltage and the low-temperature-time voltage, and corrects the concentration of the combustible gas by using the humidity.

According to the combustible gas detection device configured as described above, the ratio between the high-temperature-time voltage and the low-temperature-time voltage can be determined with high resolution. Therefore, the humidity of the object atmosphere can be calculated accurately, and the concentration of the combustible gas can be detected more accurately because the concentration is corrected by using the accurately calculated humidity.

Notably, the combustible gas detection device of the present invention can effectively provide the above-described effect when the invention is applied to the case where the combustible gas detection device includes a gas detection element which is formed from a silicon substrate through micromachining and in which the heat generation resistor and the temperature measurement resistor are disposed on the silicon substrate. Specifically, the gas detection element which is formed from a silicon substrate through micromachining is very small in size. Therefore, in the case where the heat generation resistor and the temperature measurement resistor are disposed on such a silicon substrate, the two resistors are disposed close to each other. If the present invention is applied to such a configuration, the heat generation temperature (predetermined temperature) of the heat generation resistor is switched before the error between the actual environmental temperature and the environmental temperature determined based on the temperature voltage of the temperature measurement resistor increases. As a result, the effect of decreasing the detection error of the gas concentration to the allowable range is attained satisfactorily.

The combustible gas detection device according to a third aspect of the present invention includes an average calculation section which detects at least one of the environmental temperatures obtained based on the resistance of the temperature measurement resistor, said environmental temperatures being measured in two successive periods among the predetermined periods controlled by the energization control section and calculates the average of a plurality of the environmental temperatures detected in the two successive periods. In this case, the gas concentration computation section of the combustible gas detection device uses the average of the environmental temperatures calculated by the average calculation section for computing the concentration of the combustible gas contained in the object atmosphere.

The combustible gas detection device configured as described above detects the environmental temperature in each of successive two periods and calculates the average of the detected environmental temperatures. Therefore, the environmental temperature can be detected in a state which reflects the influence on the temperature measurement resistor of the difference (change) of the heat generation amount of the heat generation resistor caused by the switching of the energization state, as compared with the case where the environmental temperature is detected only in the periods corresponding to one of the two predetermined temperatures of the heat generation resistor. Therefore, the detection accuracy of the environmental temperature can be improved.

Also, since the averaged environmental temperature is calculated, even when the value of the environmental temperature based on the temperature measurement resistor changes due to influence of unexpected noise or the like, a drop in the accuracy in detecting the concentration of the combustible gas caused by the change can be suppressed.

Therefore, according to the present invention, the detection accuracy of the environmental temperature can be improved, and a drop in the detection accuracy of the combustible gas can be suppressed.

Also, in the combustible gas detection device according to a fourth aspect of the present invention, the length of the period of time is set to fall within a range of 25 msec to 1 sec.

When the period of time is shorter than 25 msec, there is a possibility that the next period starts (in other words, the timing of switching the state of energization comes) before the time required for stabilizing the temperature of the heat generation resistor elapses after the previous switching of the state of energization of the heat generation resistor. In such a case, there is a possibility that the voltages generated across the heat generation resistor corresponding to the two predetermined temperatures cannot be detected properly.

In the case where the period of time is longer than 1 sec, the interval of the switching of the state of energization of the heat generation resistor increases, which results in an increase in the interval of the detection of the voltages generated across the heat generation resistor corresponding to the two predetermined temperatures. In such a case, the followability to a change in the gas concentration deteriorates, and the detection accuracy of the gas concentration may decrease.

Therefore, according to the combustible gas detection device of the present invention, the voltage generated across the heat generation resistor can be detected properly in the state in which the temperature of the heat generation resistor is stable, and a drop in the followability to a change in the gas concentration can be suppressed. Accordingly, a drop in the detection accuracy of the gas concentration can be suppressed.

Also, in the combustible gas detection device according to a fifth aspect of the present invention, the substrate has a rectangular shape (substantially rectangle) as viewed from above; and when the substrate is viewed from above, the heat generation resistor is disposed on the substrate at a location closer to the center thereof as compared with the temperature measurement resistor that is formed in a region which extends along at least adjacent two sides of the four sides which form the peripheral edge of the substrate.

According to the combustible gas detection device configured as described above, the region within which the temperature measurement resistor is disposed can be made relatively large. Therefore, the temperature measurement resistor can be easily designed to have a length for obtaining a resistance within a desired range, and the degree of freedom of design can be increased. In the combustible gas detection device configured as described above, when the length of the temperature measurement resistor must be increased, a portion of the temperature measurement resistor which is close to the heat generation resistor becomes larger due to the demand for reducing the size of the substrate. Therefore, the temperature measurement resistor becomes more likely to be thermally affected by the heat generation resistor. Accordingly, the gas concentration detection device according to the first aspect of the present invention can be applied more effectively.

Moreover, in the combustible gas detection device according to a sixth aspect of the present invention, the temperature measurement resistor is disposed in a region which extends along three sides of the peripheral edge of the substrate. In this case, since the region within which the temperature measurement resistor is disposed can be made large, the degree of freedom of design can be increased. In this case, a portion of the temperature measurement resistor which is close to the heat generation resistor may become larger, and the temperature measurement resistor becomes more likely to be thermally affected by the heat generation resistor. Accordingly, the gas concentration detection device according to the first aspect of the present invention can be applied much more effectively.

Notably, in the combustible gas detection device according to a seventh aspect of the present invention, a first electrode group including two electrodes connected to opposite ends of the heat generation resistor and a second electrode group including two electrodes connected to opposite ends of the temperature measurement resistor are disposed in a region which extends along one side of the peripheral edge of the substrate.

According to the combustible gas detection device configured as described above, the heat generation resistor and the temperature measurement resistor can be easily connected to an input/output circuit section provided externally of the substrate. Therefore, the wiring structure can be simplified, and the overall size of the combustible gas detection device can be decreased.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 3A and 3B are flowcharts showing the detail of gas concentration computation processing.

DETAILED DESCRIPTION OF THE INVENTION

Description of Symbols

1: combustible gas detection device; 3: gas detection element; 5: control circuit; 7: microcomputer; 8: storage device; 9: start switch; 34: heat generation resistor; 35: temperature measurement resistor; 50: energization control circuit; 51: bridge circuit; 52: variable resistor section; 55: current adjustment circuit; 57: switching circuit; 80: temperature adjustment circuit; 81: bridge circuit; 87: switching circuit; 521, 522: fixed resistor; 523: changeover switch; CH: first predetermined temperature; CL: second predetermined temperature; TW: time period.

Mode for Carrying Out the Invention

Embodiments of the present invention will now be described with reference to the drawings.

Figure 1:
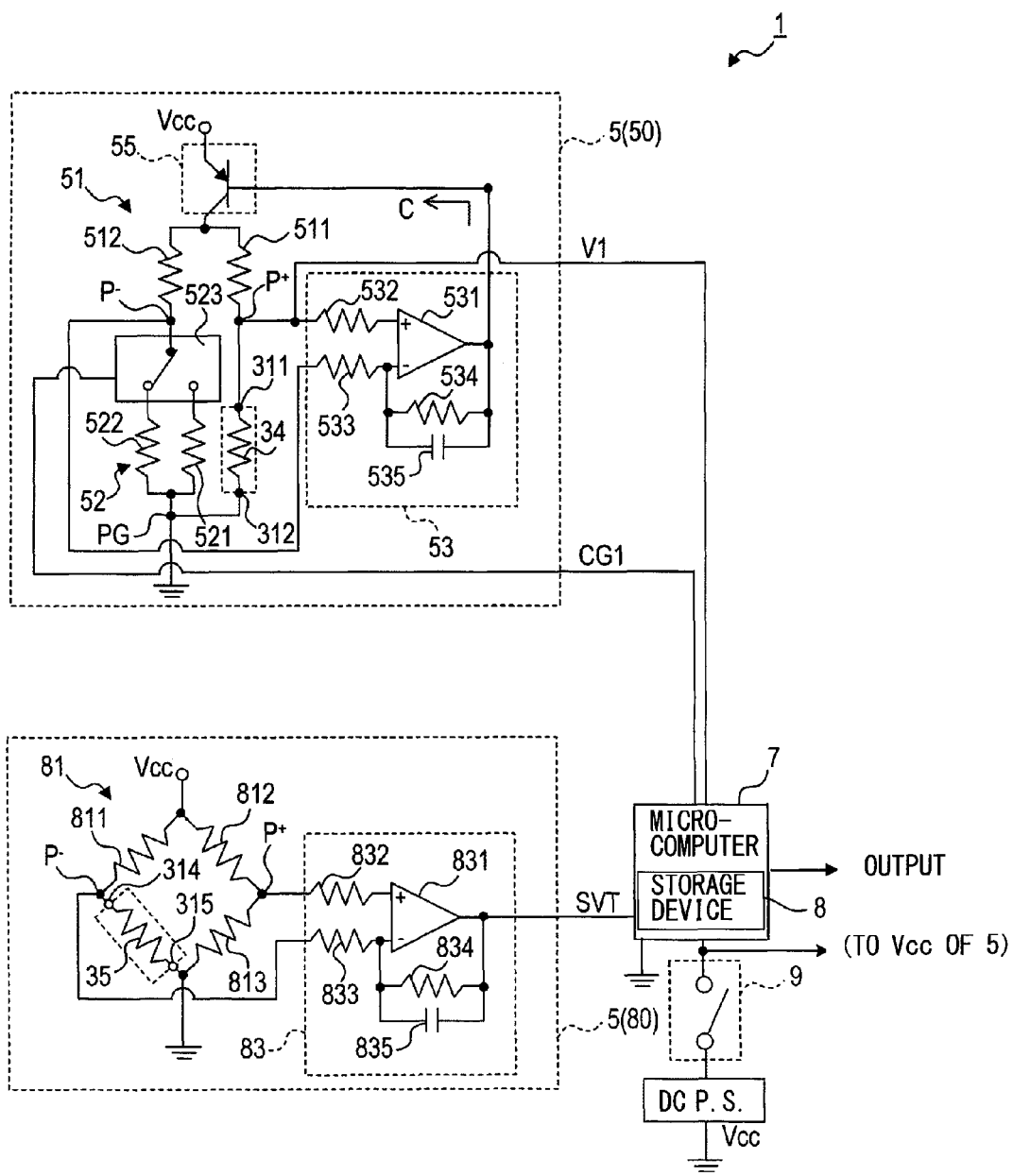
FIG. 1 is a diagram showing the overall configuration of a combustible gas detection device.
Figure 2A:
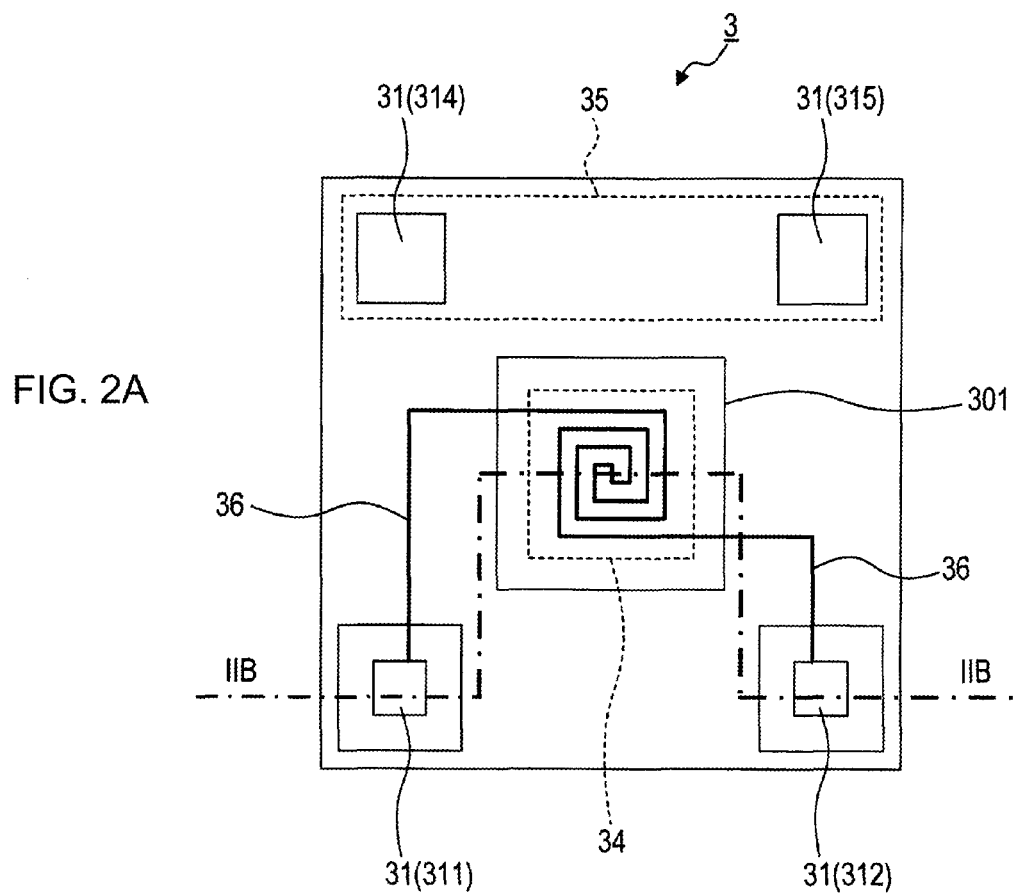
FIG. 2A is a plan view showing the structure of a gas detection element which is a main portion of the combustible gas detection device.
Figure 2B:
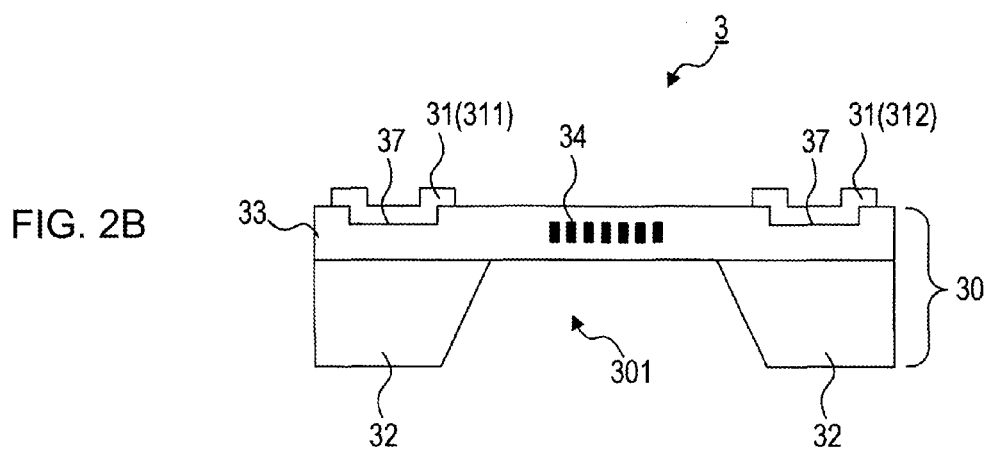
FIG. 2B is a cross-sectional view of the gas detection element taken along line in FIG. 2A.

FIG. 1 is a diagram showing the overall configuration of a combustible gas detection device 1 to which the present invention is applied. FIG. 2A is a plan view showing the structure of a gas detection element 3 which is a main portion of the combustible gas detection device 1 (the view also shows a part of the internal structure), and FIG. 2B is a cross-sectional view of the gas detection element taken along line IIB-IIB in FIG. 2A.

[Overall Configuration]

The combustible gas detection device 1, which detects the concentration of a combustible gas by using the thermal-conduction-type gas detection element 3, is disposed in, for example, the cabin of a fuel cell automobile for the purpose of, for example, detecting leakage of hydrogen.

As shown in FIG. 1, the combustible gas detection device 1 includes a control circuit 5 which drives and controls the gas detection element 3 (see FIGS. 2A and 2B); a microcomputer 7 which generates a switching signal CG1 for controlling the operation of the control circuit 5 and performs various types of processing operations including at least a processing operation of computing the concentration of a combustible gas contained in an object gas on the basis of detection signals V1 and SVT obtained from the control circuit 5 (gas concentration computation processing); and a start switch 9 which starts and stops the control circuit 5 and the microcomputer 7 by establishing and cutting off a passage for supplying electric power from a DC power supply Vcc to the combustible gas detection device 1.

The control circuit 5 (excluding a heat generation resistor 34 and a temperature measurement resistor 35 to be described later), the microcomputer 7, and the start switch 9 are formed on a single circuit board, and the gas detection element 3 is formed separately from the circuit board.

[Gas Detection Element]

Next, the gas detection element 3 will be described.

As shown in FIGS. 2A and 2B, the gas detection element 3 includes a flat base 30 (having a rectangular shape as viewed from above). A plurality of electrodes 31 are formed on one surface (hereinafter referred to as the "front surface") of the base 30, and a recess 301 is formed on the other surface (hereinafter referred to as the "back surface") of the base 30 near the center of the base 30 such that the recess 301 extends along one direction of the base 30.

The gas detection element 3 has a size of several millimeters in the length and width directions (e.g., 3 mm×3 mm), and is manufactured from a silicon substrate by using, for example, a micromachining technique (micromachining process).

The electrodes 31 includes two electrodes (electrode pads) 311 and 312 (hereinafter also referred to as the "first electrode group") disposed along one side (the lower side in FIG. 2A) of the base 30 and two electrodes (electrode pads) 314 and 315 (hereinafter also referred to as the "second electrode group") disposed along the opposite side (the upper side in FIG. 2A)

of the base 30. Of these electrodes, the electrodes 312 and 315 will be also referred to as the "ground electrodes" in the following description. The electrodes 31 are made of, for example, aluminum (Al) or gold (Au).

The base 30 includes a substrate 32 made of silicon and an insulating layer 33 formed on one surface of the substrate 32, and has a diaphragm structure. Specifically, the substrate 32 is partially removed such that the insulating layer 33 is partially exposed (through a substantially square opening in the present embodiment), whereby the above-mentioned recess 301 is formed. In the base 30, the side where the insulating layer 33 is present (where the substrate 32 is not removed) serves as the front surface of the base 30, and the side where the substrate 32 is present (including a region where the substrate 32 is partially removed) serves as the back surface of the base 30.

A spirally wound wire-shaped heat generation resistor 34 is embedded in a portion of the insulating layer 33 exposed to the back surface of the base 30 through the recess 301, and a temperature measurement resistor 35 used for temperature measurement is embedded along a long side (one side) of the base 30 on the side where the second electrode group (electrodes 314 and 315) is formed. Namely, the heat generation resistor 34 is supported by the insulating layer 33 to be located in a region closer to the center as compared with the temperature measurement resistor 35, and the temperature measurement resistor 35 is disposed in a region extending along one of the four sides which form the peripheral edge of the insulating layer 33.

The insulating layer 33 may be made of a single material or a composed of a plurality of layers made of different materials. Examples of the insulating material used for forming the insulating layer 33 include silicon oxide ($SiO_2$) and silicon nitride ($Si_3N_4$).

The heat generation resistor 34 is made of an electrically conductive material having a large temperature coefficient of resistance such that the resistance of the heat generation resistor 34 changes with the temperature of itself, and the temperature measurement resistor 35 is made of an electrically conductive material selected such that the resistance of the temperature measurement resistor 35 changes in proportion to temperature (in the present embodiment, the resistance increases as the temperature increases). The heat generation resistor 34 and the temperature measurement resistor 35 are made of the same resistor material (in the present embodiment, platinum (Pt)).

The heat generation resistor 34 is connected to the first electrode group (electrodes 311 and 312) through wiring lines 36 and wiring films 37 embedded to be located on the same plane as the plane on which the heat generation resistor 34 is formed. The temperature measurement resistor 35 is connected to the second electrode group (electrodes 314 and 315) through wiring films (not shown) embedded to be located on the same plane as the plane on which the temperature measurement resistor 35 is formed.

The wiring lines 36 and the wiring films 37 are made of the same resistor material as that used for forming the heat generation resistor 34 and the temperature measurement resistor 35. The electrodes 31 formed on the front surface of the base 30 are connected to the corresponding wiring films 37 formed within the base 30 (the insulating layer 33) through contact holes (connection conductors).

Namely, one end of the heat generation resistor 34 is connected to the electrode 311 and the other end thereof is connected to the ground electrode 312; and one end of the temperature measurement resistor 35 is connected to the electrode 314 and the other end thereof is connected to the ground electrode 315.

The gas detection element 3 configured as described above is used in a state in which the back surface on which the recess 301 is formed is exposed to an object atmosphere.

[Control Circuit]

Next, the configuration of the control circuit 5 will be described.

As shown in FIG. 1, the control circuit 5 includes an energization control circuit 50 which controls the supply of electricity to the heat generation resistor 34 (hereinafter also referred to as the "energization of the heat generation resistor 34") and outputs a detection signal V1 corresponding to the voltage across the heat generation resistor 34; and a temperature adjustment circuit 80 which supplies electricity to the temperature measurement resistor 35 and outputs a detection signal SVT which represents the temperature of the object atmosphere.

[Energization Control Circuit]

The energization control circuit 50 includes a bridge circuit (Wheatstone bridge circuit) 51 including the heat generation resistor 34; an amplification circuit 53 which amplifies the potential difference detected in the bridge circuit 51; and a current adjustment circuit 55 which adjusts (increases or decreases) the current flowing through the bridge circuit 51 in accordance with the output of the amplification circuit 53.

The current adjustment circuit 55 includes a transistor which is connected to a power line for supplying the DC power supply voltage Vcc to the bridge circuit 51 and whose conduction state (ON-resistance) changes in accordance with an adjustment signal C output from the amplification circuit 53. Specifically, when the level of the adjustment signal C increases, the ON-resistance increases, and the current flowing through the bridge circuit 51 decreases. In contrast, when the level of the adjustment signal C decreases, the ON-resistance decreases and the current flowing through the bridge circuit 51 increases.

The amplification circuit 53 includes a well known differential amplification circuit which is composed of an operation amplifier 531; fixed resistors 532 and 533 connected to the inverting input terminal and the non-inverting input terminal, respectively, of the operation amplifier 531; and a fixed resistor 534 and a capacitor 535 connected between the inverting input terminal and the output terminal of the operation amplifier 531.

Namely, when the voltage input to the non-inverting input terminal is higher than the voltage input to the inverting input terminal, the level of the adjustment signal C output from the amplification circuit 53 increases (thus, the current flowing through the bridge circuit 51 decreases); and when the voltage input to the non-inverting input terminal is lower than the voltage input to the inverting input terminal, the level of the adjustment signal C decreases (thus, the current flowing through the bridge circuit 51 increases).

The bridge circuit 51 includes the heat generation resistor 34, two fixed resistors 511 and 512, and a variable resistor section 52 whose resistance can be switched. The fixed resistor 511 and the heat generation resistor 34 are connected in series, and the fixed resistor 512 and the variable resistor section 52 are connected in series. End portions PG of the series circuits located on the side where the heat generation resistor 34 and the variable resistor section 52 are provided are grounded, and the end portions of the series circuits located on the side where the fixed resistors 511 and 512 are provided are connected to the power supply side (the current adjustment circuit 55).

A connection node P+ between the fixed resistor 511 and the heat generation resistor 34 is connected to the non-inverting input terminal of the operation amplifier 531 through the fixed resistor 532. A connection node P− between the fixed resistor 512 and the variable resistor section 52 is connected to the inverting input terminal of the operation amplifier 531 through the fixed resistor 533. The potential at the connection node P+ is also supplied to the microcomputer 7 as the detection signal V1.

The variable resistor section 52 includes two fixed resistors 521 and 522 which differ in resistance, and a changeover switch 523 which enables one of the fixed resistors 521 and 522 in accordance with the switching signal CG1 from the microcomputer 7. The balance of the bridge circuit 51 can be changed by switching the resistance of the variable resistor section 52 by the changeover switch 523.

The fixed resistor 521 has a resistance such that the temperature of the heat generation resistor 34 becomes equal to a first predetermined temperature CH (e.g., 400° C.), and the fixed resistor 522 has a resistance such that the temperature of the heat generation resistor 34 becomes equal to a second predetermined temperature CL (e.g., 300° C.) lower than the first predetermined temperature CH.

In the energization control circuit 50 configured as described above, when the supply of electricity from the DC power supply Vcc to the bridge circuit 51 is started, the amplification circuit 53 and the current adjustment circuit 55 adjust the current flowing through the bridge circuit 51 such that the potential difference between the connection nodes P+ and P− becomes zero. As a result, the resistance of the heat generation resistor 34 is controlled to a fixed value determined by the variable resistor section 52 (thus, the temperature of the heat generation resistor 34 is controlled to the first predetermined temperature CH or the second predetermined temperature CL).

Specifically, in the case where the amount of the combustible gas within the object atmosphere has changed and the amount of heat taken away by the combustible gas has become greater than the amount of heat generated by the heat generation resistor 34, the resistance of the generation resistor 34 decreases because the temperature of the heat generation resistor 34 drops. In contrast, in the case where the amount of heat taken away by the combustible gas has become smaller than the amount of heat generated by the heat generation resistor 34, the resistance of the generation resistor 34 increases because the temperature of the heat generation resistor 34 rises.

When the resistance of the generation resistor 34 decreases, the amplification circuit 53 and the current adjustment circuit 55 increase the current flowing through the bridge circuit 51 to thereby increase the amount of heat generated by the heat generation resistor 34. In contrast, when the resistance of the generation resistor 34 increases, the amplification circuit 53 and the current adjustment circuit 55 decrease the current flowing through the bridge circuit 51 to thereby decrease the amount of heat generated by the heat generation resistor 34. Thus, the heat generation resistor 34 is controlled to have a fixed (constant) resistance (accordingly, a fixed (constant) temperature).

Namely, the magnitude of the current flowing through the heat generation resistor 34; i.e., the amount of heat required to maintain constant the temperature (resistance) of the heat generation resistor 34 (further, the amount of heat taken away by the combustible gas) can be determined from the detection signal V1, which represents the potential at the connection node P+. Since the required amount of heat changes with the gas concentration, the concentration of the combustible gas can be determined from the detection signal V1. Specifically, when the gas concentration is calculated, correction is performed using the humidity H of the object atmosphere; however, this will be described in the section "gas concentration computation processing" provided below.

[Temperature Measurement Circuit]

The temperature adjustment circuit 80 includes a bridge circuit (Wheatstone bridge circuit) 81 including the temperature measurement resistor 35; and an amplification circuit 83 which amplifies the potential difference obtained from the bridge circuit 81.

The amplification circuit 83 includes a well known differential amplification circuit which is composed of an operation amplifier 831; fixed resistors 832 and 833 connected to the inverting input terminal and the non-inverting input terminal, respectively, of the operation amplifier 831; and a fixed resistor 834 and a capacitor 835 connected between the inverting input terminal and the output terminal of the operation amplifier 831.

The bridge circuit 81 includes the temperature measurement resistor 35 and three fixed resistors 811, 812, and 813. The fixed resistor 811 and the temperature measurement resistor 35 are connected in series, and the fixed resistor 812 and the fixed resistor 813 are connected in series. End portions of these series circuits located on the side where the temperature measurement resistor 35 and the fixed resistor 813 are provided are grounded, and end portions of these series circuits located on the side where the fixed resistors 811 and 812 are provided are connected to the power supply.

A connection node P− between the fixed resistor 811 and the temperature measurement resistor 35 is connected to the inverting input terminal of the operation amplifier 831 through the fixed resistor 833. A connection node P+ between the fixed resistors 812 and 813 is connected to the non-inverting input terminal of the operation amplifier 831 through the fixed resistor 832. The output of the operation amplifier 831 is also supplied to the microcomputer 7 as the temperature detection signal SVT.

The temperature measurement resistor 35 is set such that when the temperature of the object atmosphere to which the gas detection element 3 is exposed is equal to a reference temperature set in advance, the temperature detection signal SVT assumes a reference value.

When the temperature of the object atmosphere changes, the resistance of the temperature measurement resistor 35 changes. As a result, a potential difference is produced, and a voltage obtained by amplifying the potential difference is output as the temperature detection signal SVT.

Notably, when the gas detection element 3 is connected to the control circuit 5, the electrodes 31 (311, 312, 314, 315) of the gas detection element 3 are connected such that the electrode 311 is connected to the connection node P+ of the energization control circuit 50, the electrode 314 is connected to the connection node P− of the temperature adjustment circuit 80, and the ground electrodes 312 and 315 are connected to the common ground line of the control circuit 5.

[Microcomputer]

The microcomputer 7 is a well known microcomputer which includes a storage device 8 (ROM, RAM, etc.) which stores various program and data for executing the gas concentration computation processing, etc.; a CPU which executes the programs stored in the storage device 8; an IO port for inputting and outputting various signals; a timer for clocking time; etc.

Here, the signal level of the detection signal V1 detected when the temperature of the heat generation resistor 34 is the first predetermined temperature CH (400° C.) will be referred to as a high-temperature-time voltage VH1; the signal level of the detection signal V1 detected when the temperature of the heat generation resistor 34 is the second predetermined temperature CL (300° C.) will be referred to as a low-temperature-time voltage VL1; and the signal level of the temperature detection signal SVT received from the temperature adjustment circuit 80 will be referred to as a temperature voltage VT.

The storage device 8 stores at least temperature conversion data which represent the correlation between the environmental temperature T within the object atmosphere and the temperature voltage VT; humidity conversion data which represent the correlation between the humidity H of the object atmosphere and the high-temperature-time voltage VH1, the low-temperature-time voltage VL1, and the temperature voltage VT; and concentration conversion data which represent the correlation between the high-temperature-time voltage VH1 or the low-temperature-time voltage VL1 (in the present embodiment, the high-temperature-time voltage VH1 is used) and the concentration X of the combustible gas. Specifically, each conversion data set represents a conversion map, a calculation formula for conversion, or the like, which is prepared in advance on the basis of data obtained through an experiment or the like.

The humidity conversion data include voltage ratio conversion map data which represent the correlation between the environmental temperature T (thus, the temperature voltage VT) and the voltage ratio VC(0) to be described later; and humidity conversion map data which represent the correlation between the voltage ratio difference $\Delta VC$ to be described later and the humidity H. The concentration conversion data include high-temperature-time voltage conversion map data which represent the correlation between the temperature voltage VT and the high-temperature-time voltage VH1(0) to be described later; humidity voltage change conversion map data which represent the correlation between the high-temperature-time voltage VH1 and the humidity H, and the high-temperature-time voltage change $\Delta VH1(H)$ to be described later; and gas sensitivity conversion map data which represent the correlation between the temperature voltage VT and the high-temperature-time voltage VH1, and the gas sensitivity G(VT) to be described later.

When electricity is supplied from the DC power supply Vcc to the microcomputer 7 as a result of the start switch 9 being turned on, the microcomputer 7 starts its operation. The CPU of the microcomputer 7 initializes various portions thereof and then starts the gas concentration computation processing.

[Gas Concentration Computation Processing]

The gas concentration computation processing executed by the CPU of the microcomputer 7 will be described with reference to the flowcharts shown in FIGS. 3A and 3B. Notably, although the gas concentration X can be obtained by a method of obtaining the gas concentration X from the low-temperature-time voltage VL1 or the high-temperature-time voltage VH1 while using the concentration conversion data and correcting the obtained gas concentration X by the environmental temperature T obtained from the temperature voltage VT while using the temperature conversion data, here, the gas concentration X is obtained by using the humidity H in addition to the environmental temperature T.

Upon start of the execution of the present processing (the gas concentration computation processing), in step S110, the CPU obtains the low-temperature-time voltage VL1 and the high-temperature-time voltage VH1 from the energization control circuit 50, and obtains the temperature voltage VT from the temperature adjustment circuit 80.

Figure 4A:
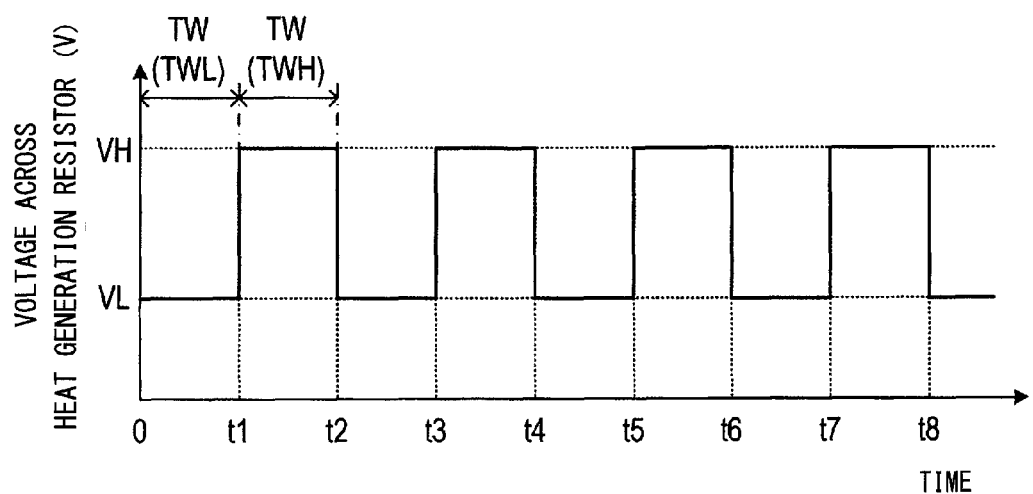
FIG. 4A is a time chart showing the voltage generated across a heat generation resistor.
Figure 4B:
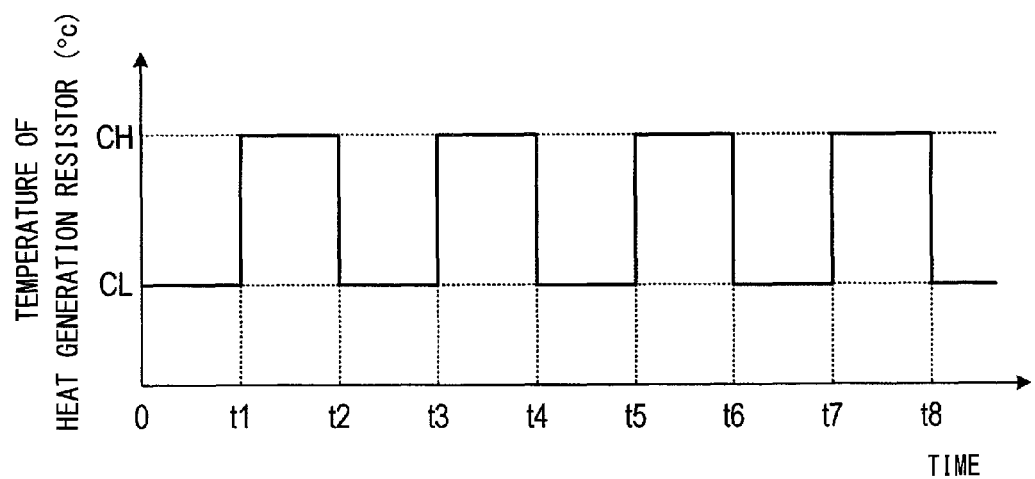
FIG. 4B is a time chart showing the temperature of the heat generation resistor.

Specifically, the CPU controls the resistance of the bridge circuit 51 by using the switching signal CG1 such that the predetermined temperature of the heat generation resistor 34 is maintained at the second predetermined temperature CL during a predetermined period of time TW (hereinafter also referred to as the "low temperature measurement period TWL"), and is then maintained at the first predetermined temperature CH during a predetermined period of time TW (hereinafter also referred to as the "high temperature measurement period TWH") by switching the setting (see FIGS. 4A and 4B). Simultaneously, the CPU detects the low-temperature-time voltage VL1 during the low temperature measurement period, detects the high-temperature-time voltage VH1 during the high temperature measurement period, and detects the temperature voltage VT in one of the two periods. FIG. 4A is a time chart showing the voltage generated across the heat generation resistor, and FIG. 4B is a time chart showing the temperature of the heat generation resistor.

In step S120, the CPU calculates the voltage ratio VC in accordance with the following equation (1) while using as input value's of the equation (1) the low-temperature-time voltage VL1 and the high-temperature-time voltage VH1 obtained in step S110.

$$VC=VH1/VL1 \quad (1)$$

In parallel therewith, in step S130, the CPU calculates the voltage ratio VC(0) at the environmental temperature T (i.e., the temperature voltage VT) for the case where the gas concentration X is zero and the humidity H is zero on the basis of the temperature voltage VT obtained in step S110 and the voltage ratio conversion map data.

In step S140, the CPU calculates the voltage ratio difference $\Delta VC$ at the environmental temperature T (i.e., the temperature voltage VT) in accordance with the following equation (2) while using as input values of the equation (2) the voltage ratio VC calculated in step S120 and the voltage ratio VC(0) calculated in step S130.

$$\Delta VC=VC-VC(0) \quad (2)$$

Next, in step S150, the CPU calculates the humidity H corresponding to the voltage ratio difference $\Delta VC$ on the basis of the voltage ratio difference $\Delta VC$ calculated in step S140 and the humidity conversion map data.

In parallel therewith, in step S160, the CPU calculates the high-temperature-time voltage VH1(0) at the environmental temperature T (i.e., the temperature voltage VT) for the case where the gas concentration X is zero and the humidity H is zero from the high-temperature-time voltage VH1 and the temperature voltage VT obtained in step S110 and the high-temperature-time voltage conversion map data.

Subsequently, in step S170, the CPU calculates a high-temperature-time voltage change $\Delta VH1(H)$, which represents a change in the high-temperature-time voltage VH1 caused by the humidity H, on the basis of the high-temperature-time voltage VH1 obtained in step S110, the humidity H calculated in step S150, and the humidity voltage change conversion map data.

In step S180, the CPU calculates a high-temperature-time voltage change $\Delta VH1(G)$, which represents a change in the high-temperature-time voltage VH1 caused by the combustible gas in accordance with the following equation (3) while using as input values of the equation (3) the high-temperature-time voltage VH1 obtained in step S110, the high-temperature-time voltage VH1(0) calculated in step S160, and the high-temperature-time voltage change $\Delta VH1(H)$ calculated in step S170.

$$\Delta VH1(G)=VH1-VH1(0)-\Delta VH1(H) \quad (3)$$

In parallel therewith, in step S190, the CPU calculates, on the basis of the high-temperature-time voltage VH1 and the temperature voltage VT obtained in step S110 and the gas sensitivity conversion map data, a gas sensitivity G(VT) which represents the sensitivity for the combustible gas (unit is the reciprocal of the gas concentration X) which is set in advance for the high-temperature-time voltage VH1, the setting being performed for each of different values of the environmental temperature T (i.e., the temperature voltage VT).

Finally, in step S200, the CPU calculates the gas concentration X (the concentration of the combustible gas) in accordance with the following equation (4) while using as input values of the equation (4) the high-temperature-time voltage change ΔVH1(G) calculated in step S180 and the gas sensitivity G(VT) calculated in step S190, and then returns to step S110.

$$X = \Delta VH1(G)/G(VT) \quad (4)$$

As described above, in the present processing, by outputting the switching signal CG1 to the changeover switch 523 every time the period of time TW elapses, the electrical path extending from the connection node P− between the fixed resistor 512 and the variable resistor section 52 to the end portion PG (the ground-side end portion of the variable resistor section 52) (the electrical path within the variable resistor section 52) is switched such that the fixed resistors 521 and 522 are alternately inserted into the electrical path. Thus, the high-temperature-time voltage VH1, the low-temperature-time voltage VL1, and the temperature voltage VT are obtained. In the gas concentration computation processing, the environmental temperature T is computed from the temperature voltage VT, the humidity H of the object atmosphere is computed from the ratio between the high-temperature-time voltage VH1 and the low-temperature-time voltage VL1, and the gas concentration X is corrected through use of the environmental temperature T and the humidity H.

Incidentally, in the present embodiment, 400° C. is employed as the first predetermined temperature CH, 300° C. is employed as the second predetermined temperature CL, the voltage generated across the heat generation resistor 34 which corresponds to 400° C. is used as the high-temperature-time voltage VH1, and the voltage generated across the heat generation resistor 34 which corresponds to 300° C. is used as the low-temperature-time voltage VL1. The reason why the difference (predetermined temperature difference) between the first predetermined temperature CH and the second predetermined temperature CL is set to 100° C. is that, in order to accurately detect the humidity H of the object atmosphere, the predetermined temperature difference must be set to 50° C. or higher so as to secure a high resolution for the ratio between the high-temperature-time voltage VH1 and the low-temperature-time voltage VL1. In consideration of the durability of the gas detection element 3 and other factors, the upper limit of the predetermined temperature difference is set to 200° C. or less, and the predetermined temperature difference is desirably set to fall within a range of 75° C. to 150° C.

Meanwhile, in order to accurately calculate the environmental temperature T within the object atmosphere, it is preferred that the temperature measurement resistor 35 be prevented to a possible degree from being affected by a change in the heat generation temperature of the heat generation resistor (i.e., the predetermined temperature difference). In particular, in the case of using the diaphragm type gas detection element 3 which is formed from the silicon substrate 32 through micromachining and in which the heat generation resistor 34 and the temperature measurement resistor 35 are embedded (disposed) in the insulating layer 33 on the substrate 32 as in the present embodiment, the heat generation resistor 34 and the temperature measurement resistor 35 are disposed close to each other because the size of the gas detection element 3 is very small. Therefore, the diaphragm type gas detection element 3 can be said to have a structure in which the temperature measurement resistor 35 is likely to be influenced by a change in the heat generation temperature of heat generation resistor 34 as described above, and it is preferred that the temperature measurement resistor 35 be prevented from being affected by such a change.

Therefore, the period of time TW during which the first or second predetermined temperature (CH, CL) is maintained (after the switching between these predetermined temperatures) must be longer than the time required for the voltage of the detection signal V1 to become stable to a sufficient degree after the switching between these predetermined temperatures. However, the period of time TW must be set such that a detection error attributable to the predetermined temperature difference of the heat generation resistor 34 at the time when the gas concentration X is detected falls within an allowable range set in advance.

The gas concentration X calculated under the assumption that the temperature measurement resistor 35 is not affected by the predetermined temperature difference of the heat generation resistor 34 stemming from the switching of the predetermined temperature (i.e., the gas concentration X calculated when the environmental temperature T fixed to a certain temperature (reference temperature)) is used as a reference concentration. If the gas concentration X determined in consideration of a change in the environmental temperature T falls within a range of ±5% F. S. (full scale) in relation to this reference concentration, the detection error is considered to fall within the allowable range.

Figure 5A:
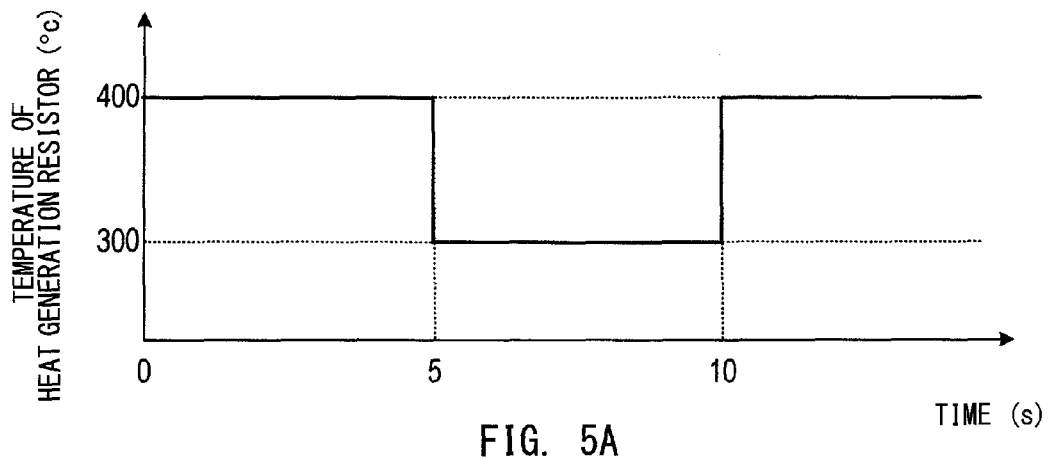
FIG. 5A is a time chart of the temperature of the heat generation resistor.
Figure 5B:
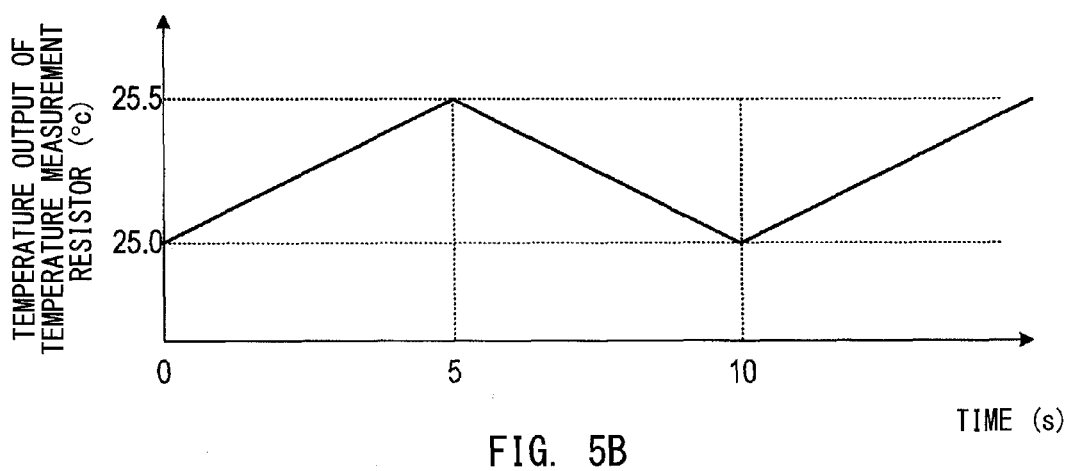
FIG. 5B is a time chart of the temperature output of a temperature measurement resistor.
Figure 5C:
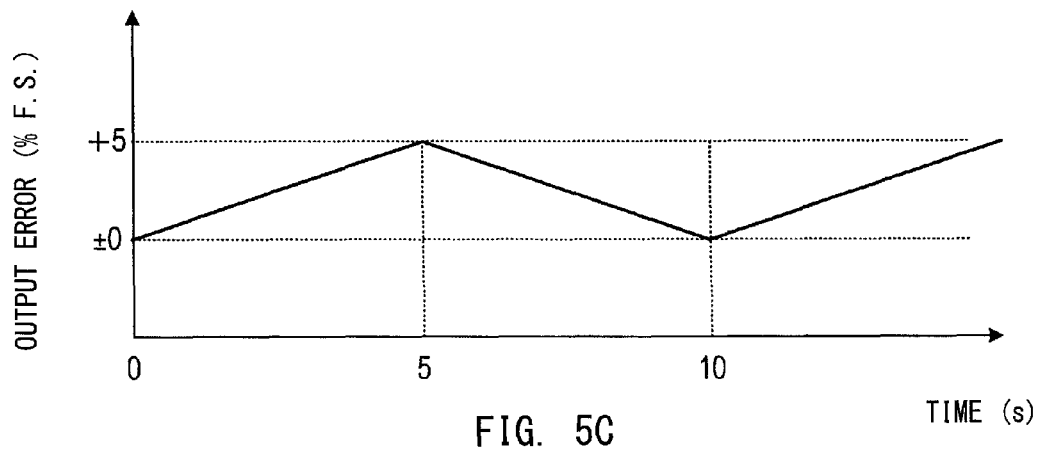
FIG. 5C is a time chart of output error.

In views of the above, a simulation for setting the period of time TM was performed by using the program of the present processing (gas concentration computation processing). FIGS. 5A, 5B, and 5C show the results of the simulation. Notably, FIGS. 5A to 5C are explanatory charts which show the results of the simulation performed for setting the period of time. Of these drawings, FIG. 5A is a time chart of the temperature of the heat generation resistor, FIG. 5B is a time chart of the temperature output of the temperature measurement resistor, and FIG. 5C is a time chart of output error.

As shown in FIGS. 5A, 5B, and 5C, in the present simulation, the period of time TW was provisionally set to 5 sec and the above-described program was executed under the condition that the environmental temperature T (reference temperature) becomes 25° C. when the predetermined temperature of the heat generation resistor 34 is 300° C., As a result of performance of the simulation, there was obtained the correlation between a change in the output of the temperature measurement resistor 35 and the output error (detection error) of the computed gas concentration X in relation to the reference concentration.

Specifically, the high-temperature-time voltage VH1, the low-temperature-time voltage VL1, and the temperature voltage VT were obtained by outputting the switching signal CG1 to the changeover switch 523 every time the period of time TW (5 sec) elapsed; the environmental temperature T was obtained from the temperature voltage VT; the humidity H of the object atmosphere was obtained from the ratio between the high-temperature-time voltage VH1 and the low-temperature-time voltage VL1; and correction was performed by using the environmental temperature T and the humidity H so as to compute the gas concentration X. A change with time of the environmental temperature T and a change with time of the output error of the computed gas concentration X in relation to the reference concentration (the gas concentration X at the reference temperature (25° C.)) were obtained as the results of the simulation.

The results of the simulation clearly show that when the period of time TW is set to 5 sec under the condition that the temperature change of the heat generation resistor 34 is 100° C. or less; the output of the temperature measurement resistor 35 changes repeatedly within a range of 0.5° C., and the output error of the gas concentration X during each period falls within the range of ±5% F. S. Namely, the correlation between the environmental temperature T and the detection error of the gas concentration X shows that if the output change of the temperature measurement resistor 35 falls within the range of 0.5° C. (in other words, within the range of ±0.5° C.), the detection error of the gas concentration X falls within the allowable range.

In this simulation, the predetermined temperature difference of the heat generation resistor 34 is set to 100° C. However, the predetermined temperature difference may be increased further in order to increase the resolution for the ratio between the high-temperature-time voltage VH1 and the low-temperature-time voltage VL1 (in other words, in order to detect the humidity H of the object atmosphere more accurately).

In this case, the temperature measurement resistor 35 becomes more likely to be influenced by a change in the heat generation temperature of the heat generation resistor 34. Therefore, the period of time TW must be shortened further such that the output change of the temperature measurement resistor 35 falls within the range of 0.5° C. In the present embodiment, the period of time TW is set to 200 ms in order to cope with various reference temperatures.

[Effects]

As described above, in the combustible gas detection device 1 of the present embodiment, the output error of the gas concentration X is decreased to fall within the range of ±5% F. S. by previously setting the period of time TW to a time determined such that the change in the environmental temperature T caused by the change in the heat generation temperature of the heat generation resistor 34 (i.e., the predetermined temperature difference) falls within the range of 0.5° C.

Therefore, according to the combustible gas detection device 1 of the present embodiment, by switching the heat generation temperature (predetermined temperature) of the heat generation resistor 34 before the error between the actual environmental temperature and the environmental temperature T based on the temperature voltage VT of the temperature measurement resistor 35 increases, the detection error of the gas concentration X (the concentration of the combustible gas) can be decreased to fall within the allowable range, and deterioration of the detection accuracy of the gas concentration X can be suppressed.

In the case of the combustible gas detection device 1, in the gas concentration computation processing, the humidity H is calculated from the high-temperature-time voltage VH1 and the low-temperature-time voltage VLA, the environmental temperature T is calculated from the temperature voltage VT, and the gas concentration X (the concentration of the combustible gas within the object atmosphere) determined on the basis of the high-temperature-time voltage VH1 is obtained (corrected) by using the humidity H and the environmental temperature T. Therefore, the gas concentration X (the concentration of the combustible gas) can be obtained accurately.

In the case of the combustible gas detection device 1, the first predetermined temperature CH and the second predetermined temperature CL are set in advance such that the predetermined temperature difference of the heat generation resistor 34 becomes 100° C., the ratio between the high-temperature-time voltage VH1 and the low-temperature-time voltage VL1 can be determined with high resolution. Therefore, the humidity H of the object atmosphere can be calculated accurately, and the gas concentration X (the concentration of the combustible gas) can be detected more accurately because the gas concentration X is corrected by using the accurately calculated humidity H.

[Correspondence to Claims]

Here, there will be described the correspondence between the sections recited in claims and the configurational elements used in the present embodiment. The energization control circuit 50 and the microcomputer 7 which outputs the switching signal CG1 correspond to the energization control section; and the microcomputer 7 which executes the gas concentration computation processing corresponds to the gas concentration computation section.

Other Embodiments

Although the embodiment of the present invention has been described, the present invention is not limited to the above-described embodiment and can be practiced in various forms without departing from the scope of the present invention.

For example, in the combustible gas detection device 1 of the above-described embodiment, the first predetermined temperature CH and the second predetermined temperature CL are set in advance such that the predetermined temperature difference of the heat generation resistor 34 becomes 100° C. However, the predetermined temperature difference is not limited to 100° C. and may be any temperature not less than 50° C. Specifically, the predetermined temperature difference is desirably set to fall within the range of 50° C. to 150° C.

In the combustible gas detection device 1 of the above-described embodiment, the period of time TW is set to 200 ms in advance. However, the period of time TW is not limited thereto and may be freely determined so long as the change in the environmental temperature T caused by the change in the heat generation temperature of the heat generation resistor 34 falls within the range of 0.5° C.

In the combustible gas detection device 1 of the above-described embodiment, the gas concentration X is calculated by using the humidity H of the object atmosphere. However, the method of calculating the gas concentration X is not limited thereto, and the embodiment may be modified such that the gas concentration X is calculated by using at least the voltages (VH1, VL1) generated across the heat generation resistor 34 and the temperature voltage VT of the temperature measurement resistor 35.

In the combustible gas detection device 1 of the above-described embodiment, the gas detection element 3 is configured such that the temperature measurement resistor 35 is disposed in a region extending along one of the four sides which form the peripheral edge of the insulating layer 33. However, the configuration of the gas detection element 3 is not limited thereto. For example, as shown in FIG. 6, the temperature measurement resistor 35 may be disposed in a region which extends along three sides of the peripheral edge of the insulating layer (a region surrounding the heat generation resistor 34) when the gas detection element 3 is viewed from the upper side thereof.

In the combustible gas detection device 1 of the above-described embodiment, the first electrode group (electrodes 311 and 312) and the second electrode group (electrodes 314 and 315) are disposed on the front surface of the base 30 along the opposite sides. However, the layout of the electrode groups is not limited thereto, and, as shown in FIG. 6, the first electrode group (electrodes 311 and 312) and the second electrode group (electrodes 314 and 315) may be disposed in a region which extends along one side of the peripheral edge of the front surface of the base 30.

Figure 6:
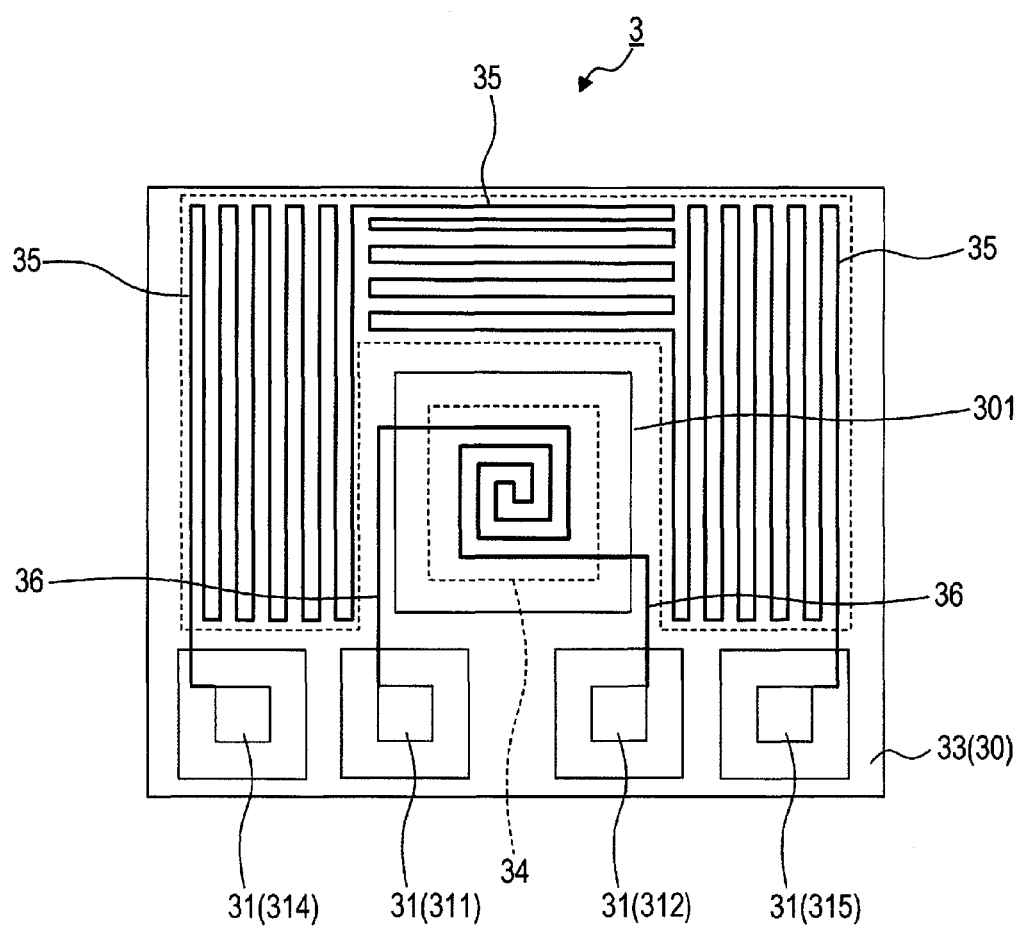
FIG. 6 is a first schematic view exemplifying the layout of various sections of the gas detection element.

Since the layout of the various sections of the gas detection element 3 shown in FIG. 6 increases the region within which the temperature measurement resistor 35 is disposed as compared with the above-described embodiment, the temperature measurement resistor 35 can be easily designed to have a length for obtaining a resistance within a desired range, and the degree of freedom of design can be increased. Also, the accuracy in detecting temperature can be increased. Moreover, since a portion of the temperature measurement resistor 35 which is close to the heat generation resistor 34 (the wiring 36) becomes larger as compared with the above-described embodiment, the temperature measurement resistor 35 becomes more likely to be thermally affected by the heat generation resistor 34. Therefore, in the case where the gas detection element 3 has such a layout; the effect—which is attained by shortening the period of time TW for switching the predetermined temperature of the heat generation resistor 34 in the gas concentration computation processing executed by the microcomputer 7 in the above-described embodiment—becomes more remarkable.

Also, since the layout of the various sections of the gas detection element 3 shown in FIG. 6 facilitates the connection between the first electrode group (electrodes 311 and 312) and the second electrode group (electrodes 314 and 315) and an input/output circuit section (e.g., a circuit board) provided externally of the gas detection element 3, the wiring structure can be simplified, and the overall size of the combustible gas detection device 1 can be decreased.

Figure 7A:
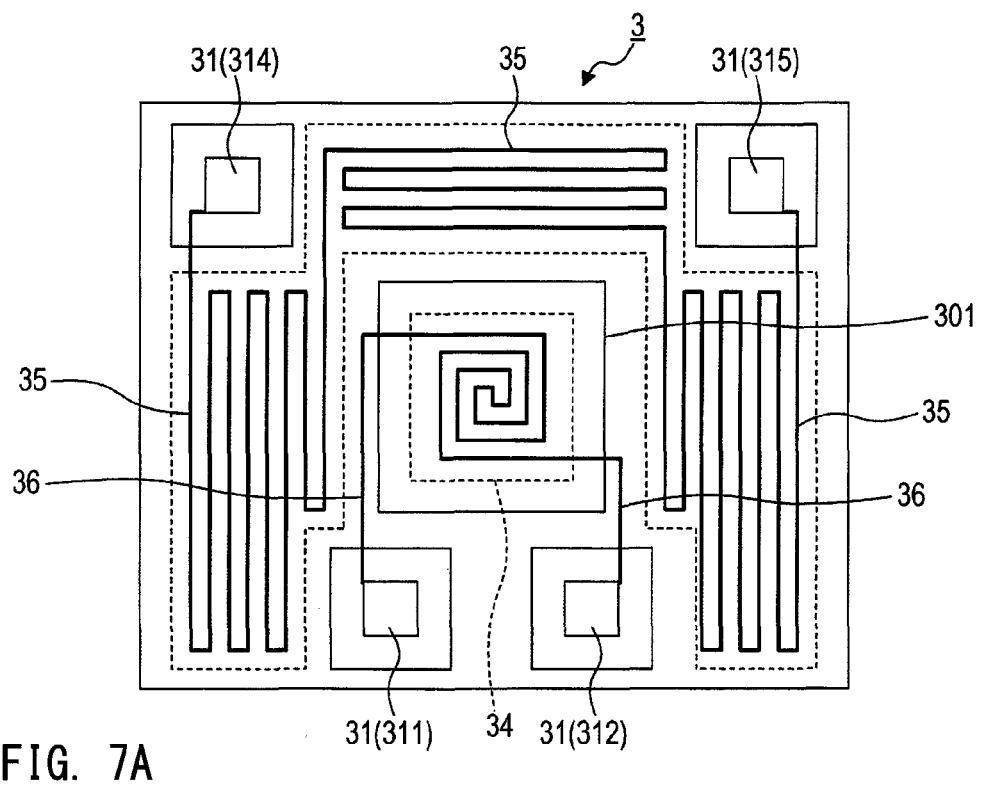
FIG. 7A is a second schematic view exemplifying the layout of various sections of the gas detection element.

The layout of the various sections of the gas detection element 3 is not limited to that shown in FIG. 6, and may be modified as shown in FIG. 7A. In this example, the first electrode group (electrodes 311 and 312) and the second electrode group (electrodes 314 and 315) are disposed on the base 30 along the opposite sides thereof, and the temperature measurement resistor 35 is disposed in a region which extends along three sides of the peripheral edge of the base 30 (a region which surrounds the heat generation resistor 34 and the first electrode group (electrodes 311 and 312)).

Figure 7B:
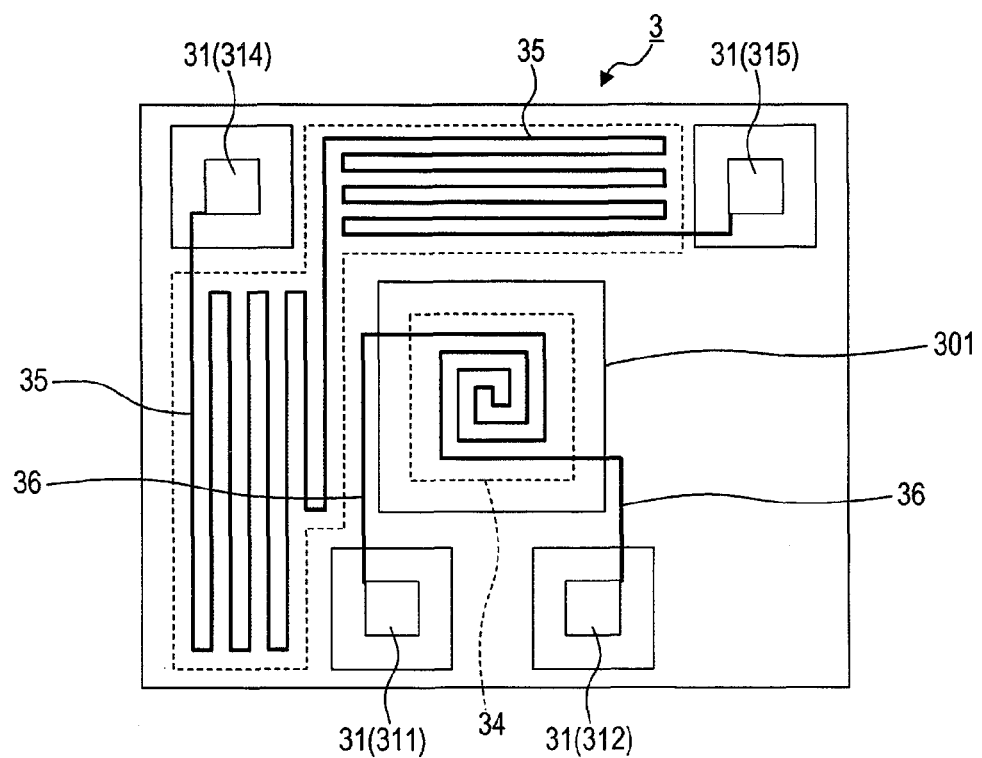
FIG. 7B is a third schematic view exemplifying the layout of various sections of the gas detection element.

Alternatively, the layout of the various sections of the gas detection element 3 may be modified as shown in FIG. 7B. In this example, the temperature measurement resistor 35 is disposed in a region which extends along two adjacent sides of the peripheral edge of the base 30 (a region which surrounds the heat generation resistor 34 and the first electrode group (electrodes 311 and 312)).

In the layout of the various sections of the gas detection element 3 shown in FIG. 2A, the distance between the heat generation resistor 34 and the temperature measurement resistor 35 when the gas detection element 3 is viewed from the upper side is set to 0.6 mm. The gas detection element 3 having such a structure enables the temperature measurement resistor 35 to properly detect the temperature in the vicinity of the heat generation resistor 34.

Although both of the heat generation resistor 34 and the temperature measurement resistor 35 are disposed in the insulating layer 33, they may be disposed at different positions in the thickness direction of the insulating layer 33 in some cases. However, since the insulating layer 33 is thin film and has a small thickness, the actual distance between the heat generation resistor 34 and the temperature measurement resistor 35 becomes substantially equal to the distance between the heat generation resistor 34 and the temperature measurement resistor 35 when the gas detection element 3 is viewed from the upper side.

The distance between the heat generation resistor 34 and the temperature measurement resistor 35 is the distance between a heating wire which constitutes the heat generation resistor 34 and a heating wire which constitutes the temperature measurement resistor 35 and is not the distance between the wiring lines (lead portions) connected to these heating wires.

The distance between the heat generation resistor 34 and the temperature measurement resistor 35 when the gas detection element 3 is viewed from the upper side is not limited to 0.6 mm so long as the distance is not greater than 1.0 mm. This enables the temperature measurement resistor 35 to properly detect the temperature in the vicinity of the heat generation resistor 34.

In the above-described embodiment, the temperature voltage VT is detected in one of the low temperature measurement period TWL and the high temperature measurement period TWH. However, the temperature voltage VT may be detected in both of the low temperature measurement period TWL and the high temperature measurement period TWH.

In view of this, a combustible gas detection device which detects the temperature voltage VT (i.e., the environmental temperature T) in each of two successive periods (the low temperature measurement period and the high temperature measurement period) and averages them to obtain the averaged temperature voltage VTav will be described as a second embodiment.

The combustible gas detection device of the second embodiment is identical in configuration with the combustible gas detection device 1 of the above-described embodiment although the processing executed by the microcomputer 7 partially differs from that in the above-described embodiment. Therefore, in the following description, the difference will be mainly described, and the description of the configuration, etc. identical with those of the first embodiment will be omitted or simplified.

The microcomputer 7 provided in the combustible gas detection device of the second embodiment starts its operation when electricity is supplied thereto from the DC power supply Vcc as a result of the start switch 9 being turned on. The microcomputer 7 first initializes various portions thereof, and then starts voltage detection processing and gas concentration computation processing.

The voltage detection processing executed by the CPU of the microcomputer 7 will be described with reference to the flowcharts shown in FIGS. 8A and 8B.

Figure 8A:
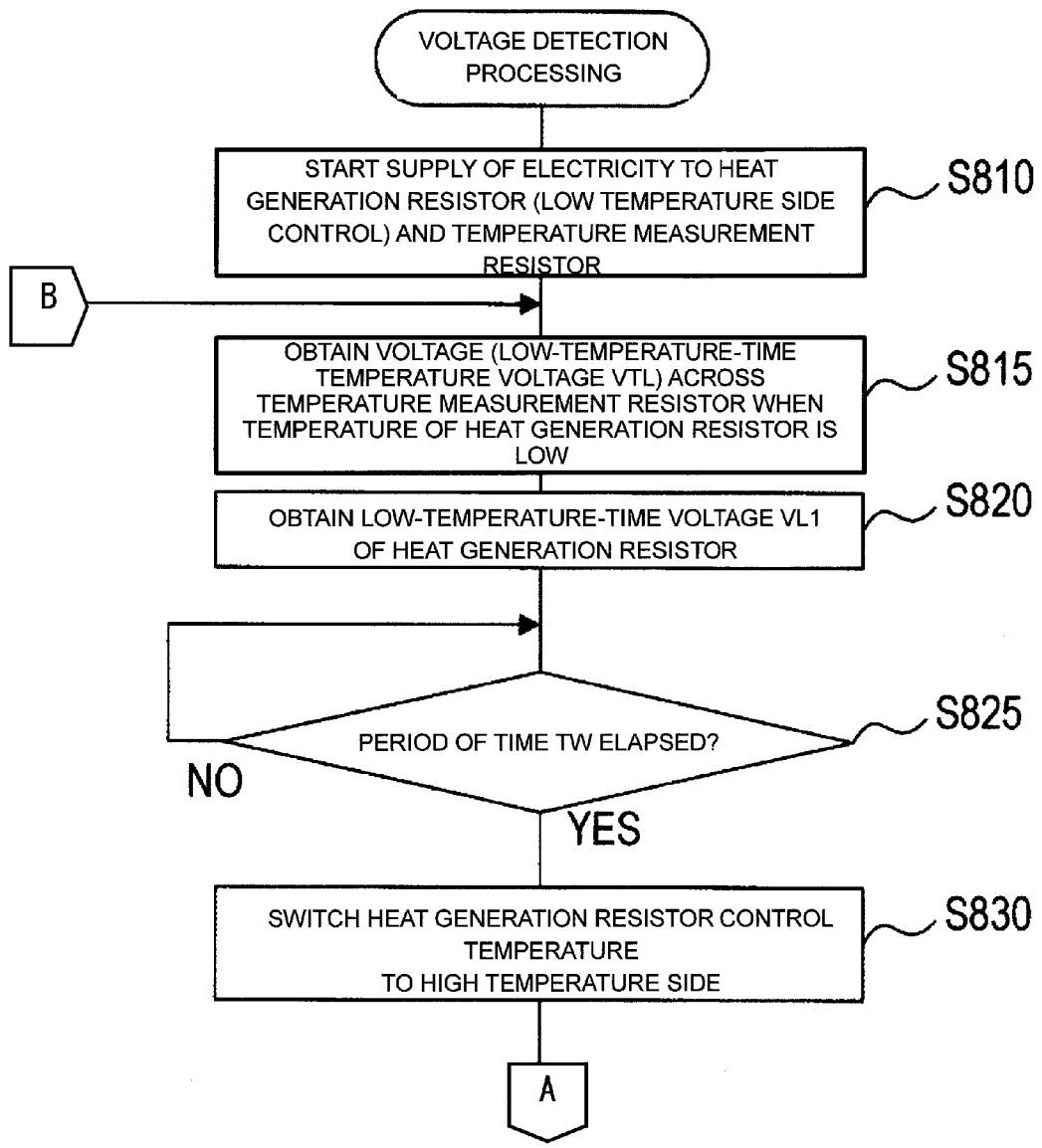
FIGS. 8A and 8B are flowcharts showing the detail of voltage detection processing in a second embodiment.
Figure 8B:
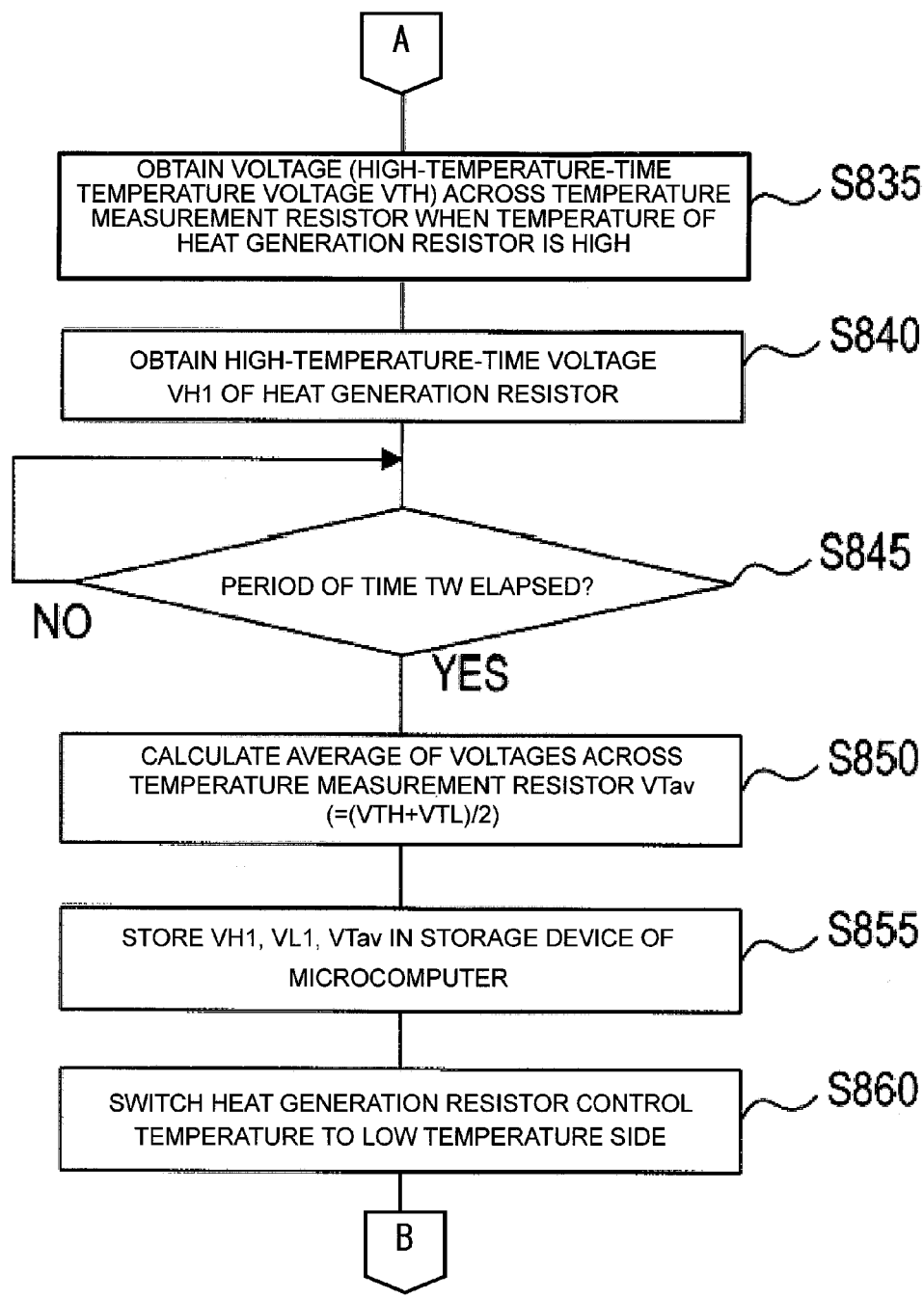

After starting the execution of the voltage detection processing shown in FIGS. 8A and 8B, the CPU first starts the supply of electricity to the heat generation resistor 34 and the temperature measurement resistor 35 in step S810.

At that time, the CPU sets the state of energization of the heat generation resistor 34 to a low-temperature-side control state. Specifically, the CPU sets the predetermined temperature of the heat generation resistor 34 in the bridge circuit 51 to the second predetermined temperature CL (300° C.) by switching the resistance of the variable resistor section 52 using the switching signal CG1.

In the next step S815, the CPU obtains the temperature voltage VT (hereinafter also referred to as the "low-temperature-time temperature voltage VTL") which is measured when the temperature of the heat generation resistor 34 is low (i.e., when the predetermined temperature of the heat generation resistor 34 is the second predetermined temperature CL).

In step S820 subsequent thereto, the CPU obtains the voltage generated across the heat generation resistor 34 (hereinafter also referred to as the "low-temperature-time voltage VL1) which is measured when the temperature of the heat generation resistor 34 is low (i.e., when the predetermined temperature of the heat generation resistor 34 is the second predetermined temperature CL).

In step S825 subsequent thereto, the CPU determines whether or not the predetermined period of time TW has elapsed after the previous switching of the state of energization of the heat generation resistor 34. When the CPU determines that the period of time TW has elapsed (affirmative determination), the CPU proceeds to step S830. When the CPU determines that the period of time TW has not yet elapsed (negative determination), the CPU repeats the processing of step S825. Thus, the CPU waits until the period of time TW elapses.

When the CPU proceeds to step S830 as a result of the affirmative determination in step S825, the CPU performs processing of switching the state of energization of the heat generation resistor 34 to a high-temperature-side control state in S830.

Specifically, the CPU sets the predetermined temperature of the heat generation resistor 34 in the bridge circuit 51 to the first predetermined temperature CH (400° C.) by switching the resistance of the variable resistor section 52 using the switching signal CG1.

In the next step S835, the CPU obtains the temperature voltage VT (hereinafter also referred to as the "high-temperature-time temperature voltage VTH") which is measured when the temperature of the heat generation resistor 34 is high (i.e., when the predetermined temperature of the heat generation resistor 34 is the first predetermined temperature CH).

In step S840 subsequent thereto, the CPU obtains the voltage generated across the heat generation resistor 34 (hereinafter also referred to as the "high-temperature-time voltage VH1) which is measured when the temperature of the heat generation resistor 34 is high (i.e., when the predetermined temperature of the heat generation resistor 34 is the first predetermined temperature CH).

In step S845 subsequent thereto, the CPU determines whether or not the predetermined period of time TW has elapsed after the previous switching of the state of energization of the heat generation resistor 34. When the CPU determines that the period of time TW has elapsed (affirmative determination), the CPU proceeds to step S850. When the CPU determines that the period of time TW has not yet elapsed (negative determination), the CPU repeats the processing of step S845. Thus, the CPU waits until the period of time TW elapses.

When the CPU proceeds to step S850 as a result of the affirmative determination in step S845, the CPU calculates the average of the temperature voltages VT (hereinafter also referred to as the "averaged temperature voltage VTav").

Specifically, the CPU calculates the average of the low-temperature-time temperature voltage VTL obtained in step S815 and the high-temperature-time temperature voltage VTH obtained in step S835 as the averaged temperature voltage VTav (=(VTL+VTH)/2).

In step S855 subsequent thereto, the CPU performs processing of storing in the storage device 8 (memory, RAM, etc.) of the microcomputer 7 the low-temperature-time voltage VL1 obtained in step S820, the high-temperature-time voltage VH1 obtained in step S840, and the averaged temperature voltage VTav calculated in S845.

In the next step S860, the CPU sets the state of energization of the heat generation resistor 34 to the low-temperature-side control state. Specifically, the CPU sets the predetermined temperature of the heat generation resistor 34 in the bridge circuit 51 to the second predetermined temperature CL (300° C.) by switching the resistance of the variable resistor section 52 using the switching signal CG1.

Upon completion of the processing of step S860, the CPU again proceeds to step S815, and repeatedly executes the processing of steps S815 to S860 until the CPU stops the voltage detection processing.

As a result of execution of the voltage detection processing, the predetermined temperature of the heat generation resistor 34 of the bridge circuit 51 is maintained at the second predetermined temperature CL during a predetermined period of time TW (hereinafter also referred to as the "low temperature measurement period TWL"), and the predetermined temperature of the heat generation resistor 34 is switched to the first predetermined temperature CH after the end of the low temperature measurement period TWL. Subsequently, the predetermined temperature of the heat generation resistor 34 is maintained at the first predetermined temperature CH during a predetermined period of time TW (hereinafter also referred to as the "high temperature measurement period TWH"), and the control for switching the predetermined temperature of the heat generation resistor 34 to the second predetermined temperature CL is performed after the end of the high temperature measurement period TWH (see FIGS. 4A and 4B).

In parallel therewith, averaging processing is performed for the temperature voltage VT. Specifically, the low-temperature-time temperature voltage VTL and the high-temperature-time temperature voltage VTH are detected, and the averaged temperature voltage VTav, which is the average of these temperature voltages, is calculated.

Namely, as a result of execution of the voltage detection processing, the state of energization of the heat generation resistor is switched every time the predetermined period of time TW elapses, and the low-temperature-time voltage VL1, the high-temperature-time voltage VH1, and the averaged temperature voltage VTav are stored in the storage device 8 (memory, RAM, etc.) of the microcomputer 7.

Next, the gas concentration computation processing in the second embodiment will be described.

Figure 9A:
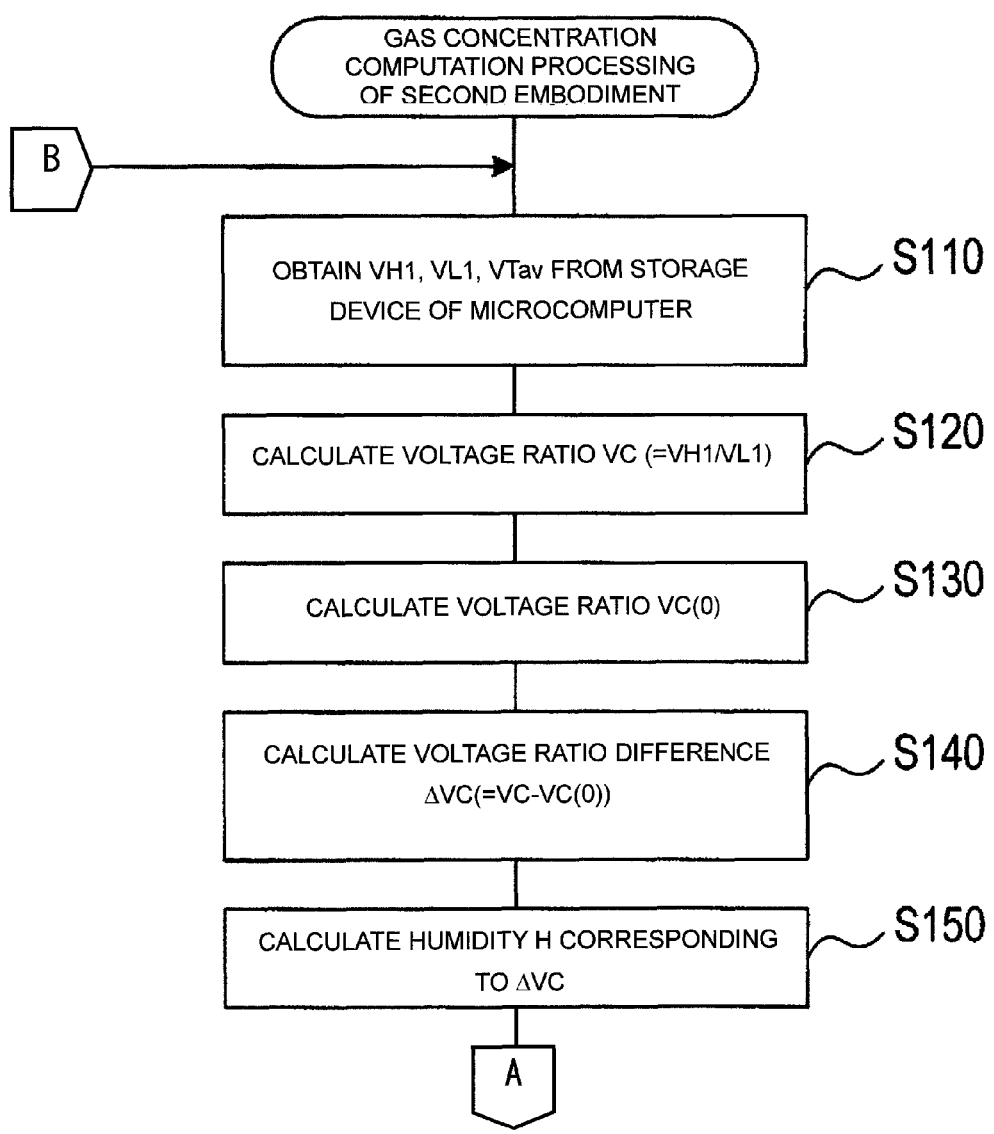
FIGS. 9A and 9B are flowcharts showing the detail of gas concentration computation processing in the second embodiment.
Figure 9B:
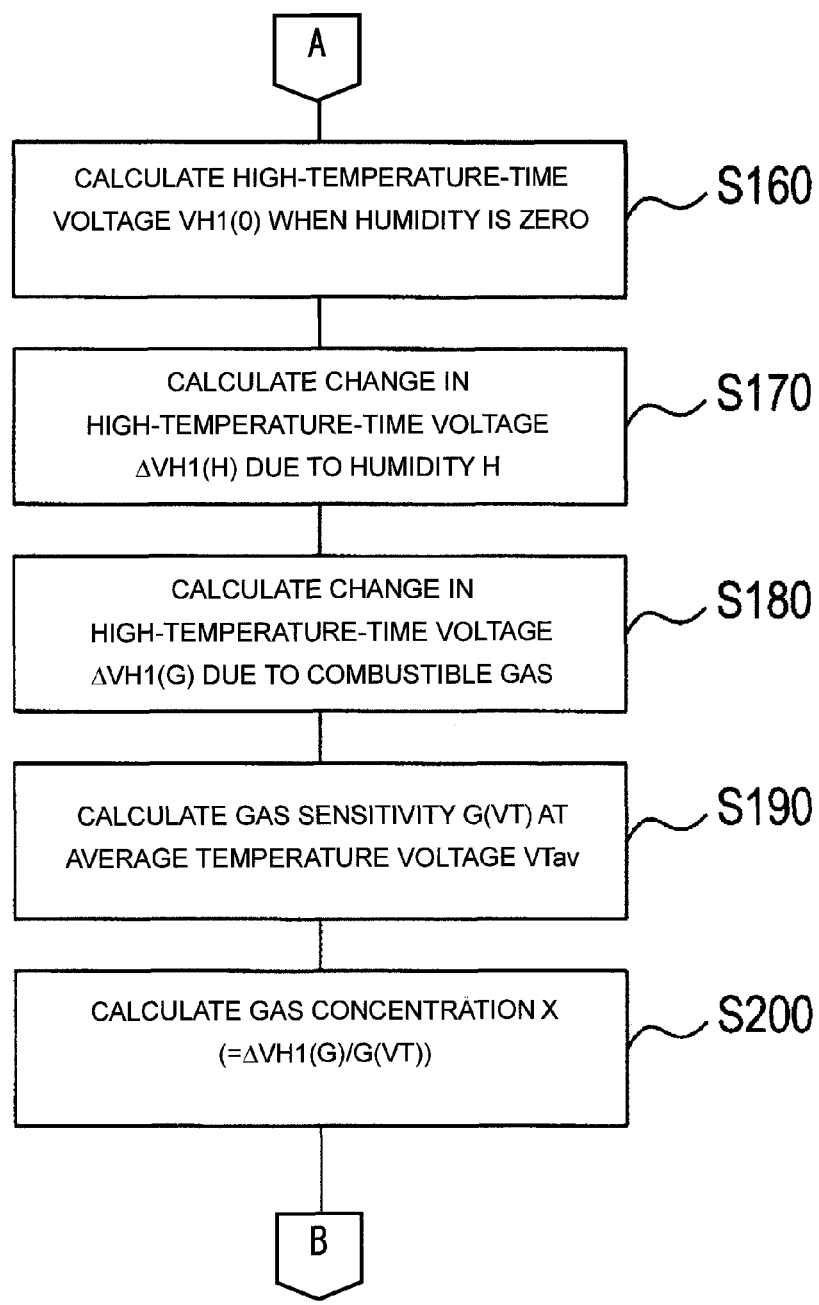

FIGS. 9A and 9B are flowcharts showing the detail of gas concentration computation processing of the second embodiment.

The gas concentration computation processing of the second embodiment differs from that of the first embodiment shown in FIGS. 3A and 3B in the contents of the processing of at least steps S110, S130, S160, and S190.

In step S110 of the second embodiment, the CPU obtains the latest values of the low-temperature-time voltage VL1, the high-temperature-time voltage VH1, and the averaged temperature voltage VTav among the information stored in the storage device 8 (memory, RAM, etc.) of the microcomputer 7. Namely, in step S110 of the second embodiment, the CPU obtains the information stored in the storage device 8 rather than obtaining various pieces of information directly from the energization control circuit 50 and the temperature adjustment circuit 80.

In step S110, the CPU obtains the averaged temperature voltage VTav rather than the temperature voltage VT. Therefore, in the remaining portion of the gas concentration computation processing of the second embodiment, unlike the first embodiment, the CPU executes various computations while using the averaged temperature voltage VTav in place of the temperature voltage VT. Namely, in steps S130, S160, and S190 of the second embodiment, the CPU executes various computations using the averaged temperature voltage VTav.

As described above, in the gas concentration computation processing of the second embodiment, the CPU first obtains the latest values of the low-temperature-time voltage VL1, the high-temperature-time voltage VH1, and the averaged temperature voltage VTav, which are stored in the storage device 8 (memory, RAM, etc.) of the microcomputer 7 as a result of execution of the voltage detection processing. In the gas concentration computation processing, the CPU computes the environmental temperature T from the averaged temperature voltage VTav, computes the humidity H of the object atmosphere from the ratio between the high-temperature-time voltage VH1 and the low-temperature-time voltage VL1, and corrects the gas concentration X by using the environmental temperature T and the humidity H.

As having been described above, in the combustible gas detection device 1 of the second embodiment, since the changeover switch 523 of the energization control circuit 50 is switched on the basis of the switching signal CG1 from the microcomputer 7, periods (cycles) corresponding to the low temperature measurement period TWL and periods (cycles) corresponding to the high temperature measurement period TWH are alternately produced every time the predetermined period of time TW elapses (S825, S830, S845, S860). The temperature voltage VT (specifically, the low-temperature-time temperature voltage VTL and the high-temperature-time temperature voltage VTH) is detected in each of successive two periods of the periods corresponding to the low temperature measurement period TWL and the high temperature measurement period TWH, and the averaged temperature voltage VTav, which is the average of these temperature voltages, is calculated (S825, S830, S845, S860). The averaged temperature voltage VTav calculated in this manner is used for computation of the concentration of the combustible gas in the gas concentration computation processing.

In the combustible gas detection device 1 having the above-described configuration, the temperature voltage VT (i.e., the environmental temperature T) can be detected in a state which reflects the influence on the temperature measurement resistor 35 of the difference of the heat generation amount of the heat generation resistor 34 caused by the switching of the energization state, unlike the case where the temperature voltage VT is detected only in the periods corresponding to the low temperature measurement period TWL or the periods corresponding to the high temperature measurement period TWH.

Namely, in the case where the predetermined temperature of the heat generation resistor 34 is switched between the two predetermined temperatures (the first predetermined temperature CH and the second predetermined temperature CL), the influence on the temperature measurement resistor 35 of the heat generation amount of the heat generation resistor 34 when the predetermined temperature of the heat generation resistor 34 is the first predetermined temperature CH differs from the influence on the temperature measurement resistor 35 of the heat generation amount of the heat generation resistor 34 when the predetermined temperature of the heat generation resistor 34 is the second predetermined temperature CL. Namely, in the case where the temperature voltage VT (i.e., the environmental temperature T) is detected only in the periods corresponding to one of the two predetermined temperatures, in the periods corresponding to the other of the two predetermined temperatures, the temperature voltage VT (i.e., the environmental temperature T) is detected in a state in which the influence on the temperature measurement resistor 35 of the heat generation amount of the heat generation resistor 34 is not reflected.

In contrast, in the case where the temperature voltage VT (i.e., the environmental temperature T) is detected in successive two periods and the averaged temperature voltage VTav, which is the average of the temperature voltages obtained in the two periods, is calculated as in the second embodiment, the temperature voltage VT (i.e., the environmental temperature T) can be detected in a state which reflects the influence on the temperature measurement resistor 35 of the difference of the heat generation amount of the heat generation resistor 34 caused by the switching of the energization state. Therefore, the detection accuracy of the environmental temperature T can be improved.

Also, the averaged temperature voltage VTav (the averaged environmental temperature), which is the average of the temperature voltages VT (i.e., the environmental temperatures T), is calculated. Therefore, even in the case where the value of the temperature voltages VT (i.e., the environmental temperatures T) based on the temperature measurement resistor 35 changes due to influence of unexpected noise or the like, a drop in the accuracy in detecting the concentration of the combustible gas caused by the change can be suppressed.

Therefore, according to the second embodiment, the detection accuracy of the environmental temperature T can be improved, and a drop in the detection accuracy of the combustible gas can be suppressed.

Here, there will be described the correspondence between the sections recited in claims and the configurational elements used in the second embodiment. The energization control circuit 50 and the microcomputer 7 which executes the steps S810, S825, S830, S845, and S860 of the voltage detection processing correspond to the energization control section; the microcomputer 7 which executes the voltage detection processing and the gas concentration computation processing corresponds to the gas concentration computation section; and the microcomputer 7 which executes the steps S815, S835, and S850 of the voltage detection processing corresponds to the average calculation section.

Although the second embodiment of the present invention has been described, the present invention is not limited to the above-described second embodiment and can be practiced in various forms without departing from the scope of the present invention.

For example, the frequency of detection of the temperature voltage VT (the low-temperature-time temperature voltage VTL or the high-temperature-time temperature voltage VTH) is not limited to that employed in the second embodiment (i.e., one time per period (period of time TW), and the temperature voltage VT may be detected two or more times in each period (period of time TW). In the case where the frequency of detection of the temperature voltage VT (the low-temperature-time temperature voltage. VTL or the high-temperature-time temperature voltage VTH is detected two or more times in each period (period of time TW), the averages of all the detected temperature voltages VT (the low-temperature-time temperature voltages VTL or the high-temperature-time temperature voltages VTH) is calculated as the averaged temperature voltage VTav (averaged environmental temperature).

The length of the period of time TW is not limited to that employed in the above-described first and second embodiments, and may be freely set within the range of 25 msec to 1 sec.

When the period of time TW is shorter than 25 msec, there is a possibility that the next period starts (in other words, the timing of switching the state of supply of electricity comes) before the time required for stabilizing the temperature of the heat generation resistor 34 elapses after the previous switching of the state of energization of the heat generation resistor 34. In such a case, there is a possibility that the voltages generated across the heat generation resistor 34 (the high-temperature-time voltage VH1 and the low-temperature-time voltage VL1) corresponding to the two predetermined temperatures (the first predetermined temperature CH and the second predetermined temperature CL) cannot be detected properly.

In the case where the period of time is longer than 1 sec, the interval of the switching of the state of energization of the heat generation resistor 34 increases, which results in an increase in the interval of the detection of the voltages generated across the heat generation resistor 34 (the high-temperature-time voltage VH1 and the low-temperature-time voltage VL1) corresponding to the two predetermined temperatures (the first predetermined temperature CH and the second predetermined temperature CL). In such a case, the followability to a change in the gas concentration may deteriorate, and the detection accuracy of the gas concentration may drop.

Therefore, according to the combustible gas detection device in which the period of time TW is set to fall within the range of 25 msec to 1 sec, the voltage generated across the heat generation resistor 34 can be detected properly in the state in which the temperature of the heat generation resistor 34 is stable, and a drop in the followability to a change in the gas concentration can be suppressed. Accordingly, a drop in the detection accuracy of the gas concentration can be suppressed.

Notably, as can be understood from the results of the simulation shown in FIGS. 5A to 5C, even in the case where the period of time TW is provisionally set to 5 sec, the output error of the gas concentration X falls within the range of ±5% F. S. Therefore, in the case where the period of time is set to 1 sec or less, the output error of the gas concentration X becomes sufficiently small, and a drop in the gas detection accuracy can be suppressed.

The device of the microcomputer 7 which stores various programs and data for executing various processing operations is not limited to the storage device 8 provided in the microcomputer 7, and may be an external storage device or a recording medium which can exchange information with the microcomputer 7. In this case, the microcomputer 7 executes the various processing operations while using the programs and data read out from the external storage device or the recording medium. Examples of the recording medium include a transportable semiconductor memory (e.g., USB memory, memory card (registered trademark), etc.), optical discs such as CD-ROM and DVD, magnetic discs, etc.

The invention claimed is:

1. A combustible gas detection device comprising:
a heat generation resistor disposed in an object atmosphere where its resistance changes with its own temperature;
an energization control section which controls the switching of an energization state of the heat generation resistor every time a predetermined time period elapses such that the heat generation resistor alternately has resistances corresponding to two predetermined temperatures set in advance;
a temperature measurement resistor disposed on a substrate having the heat generation resistor disposed thereon where its resistance changes with an environmental temperature which is the temperature of the object atmosphere;
a gas concentration computation section which calculates a concentration of a combustible gas contained in the object atmosphere by using a voltage generated across the heat generation resistor which is detected when electricity is supplied to the heat generation resistor by the energization control section, and using the environmental temperature based on a voltage change which occurs as a result of a change in the resistance of the temperature measurement resistor, wherein
the period of time has a length determined in advance such that a change in the environmental temperature which occurs when the energization control section switches the energization state of the heat generation resistor falls within a range of 0.5° C.

2. The combustible gas detection device according to claim 1, wherein
the two predetermined temperatures are preset to be a first predetermined temperature and a second predetermined temperature,
the second predetermined temperature is lower than the first set temperature,
the first and second predetermined temperatures are preset in advance such that the difference between the first and second predetermined temperatures becomes 50° C. or greater; and
the gas concentration computation section determines the voltage across the heat generation resistor detected at the first predetermined temperature as a high-temperature-time voltage, determines the voltage across the heat generation resistor detected at the second predetermined temperature as a low-temperature-time voltage, calculates a humidity of the object atmosphere based on a ratio between the high-temperature-time voltage and the low-temperature-time voltage, and corrects the concentration of the combustible gas by using the humidity.

3. The combustible gas detection device according to claim 2, further comprising:
an average calculation section which detects at least one of environmental temperatures obtained based on the resistance of the temperature measurement resistor, said environmental temperatures being measured in two successive periods among the predetermined time periods controlled by the energization control section and calculates an average of a plurality of the environmental temperatures detected in the two successive periods, wherein
the gas concentration computation section uses the average of the environmental temperatures calculated by the average calculation section for computing the concentration of the combustible gas contained in the object atmosphere.

4. The combustible gas detection device according to claim 2, wherein the length of the predetermined time period is set to fall within a range of 25 msec to 1 sec.

5. The combustible gas detection device according to claim 2, wherein
the substrate has a rectangular shape as viewed from above; and
when the substrate is viewed from above, the heat generation resistor is disposed on the substrate at a location closer to the center thereof as compared with the temperature measurement resistor that is formed in a region which extends along at least adjacent two sides of four sides which form a peripheral edge of the substrate.

6. The combustible gas detection device according to claim 1, further comprising:
an average calculation section which detects at least one of environmental temperatures obtained based on the resistance of the temperature measurement resistor, said environmental temperatures being measured in two successive periods among the predetermined time periods controlled by the energization control section and calculates an average of a plurality of the environmental temperatures detected in the two successive periods, wherein
the gas concentration computation section uses the average of the environmental temperatures calculated by the average calculation section for computing the concentration of the combustible gas contained in the object atmosphere.

7. The combustible gas detection device according to claim 6, wherein the length of the predetermined time period is set to fall within a range of 25 msec to 1 sec.

8. The combustible gas detection device according to claim 6, wherein
the substrate has a rectangular shape as viewed from above; and
when the substrate is viewed from above, the heat generation resistor is disposed on the substrate at a location closer to the center thereof as compared with the temperature measurement resistor that is formed in a region which extends along at least adjacent two sides of four sides which form a peripheral edge of the substrate.

9. The combustible gas detection device according to claim 1, wherein the length of the predetermined time period is set to fall within a range of 25 msec to 1 sec.

10. The combustible gas detection device according to claim 9, wherein
the substrate has a rectangular shape as viewed from above; and
when the substrate is viewed from above, the heat generation resistor is disposed on the substrate at a location closer to the center thereof as compared with the temperature measurement resistor that is formed in a region which extends along at least adjacent two sides of four sides which form a peripheral edge of the substrate.

11. The combustible gas detection device according to claim 1, wherein
the substrate has a rectangular shape as viewed from above; and
when the substrate is viewed from above, the heat generation resistor is disposed on the substrate at a location closer to the center thereof as compared with the temperature measurement resistor that is formed in a region which extends along at least adjacent two sides of four sides which form a peripheral edge of the substrate.

12. The combustible gas detection device according to claim 11, wherein the temperature measurement resistor is disposed in a region which extends along three sides of the peripheral edge of the substrate.

13. The combustible gas detection device according to claim 12, wherein a first electrode group including two electrodes connected to opposite ends of the heat generation resistor and a second electrode group including two electrodes connected to opposite ends of the temperature measurement resistor, are disposed in a region which extends along one side of the peripheral edge of the substrate.

* * * * *